US011529524B2

(12) United States Patent
Lehmann et al.

(10) Patent No.: US 11,529,524 B2
(45) Date of Patent: Dec. 20, 2022

(54) ENCAPSULATED ELECTRONIC CIRCUIT

(71) Applicants: Torsten Lehmann, Earlwood (AU);
Gregg Jørgen Suaning, Lisarow (AU);
Tony Mikael Nygard, Terrigal (AU);
Thomas Guenther, Tiefenbronn (DE);
William Lim, Gordon (AU); Kushal Das, Kensington (AU)

(72) Inventors: Torsten Lehmann, Earlwood (AU);
Gregg Jørgen Suaning, Lisarow (AU);
Tony Mikael Nygard, Terrigal (AU);
Thomas Guenther, Tiefenbronn (DE);
William Lim, Gordon (AU); Kushal Das, Kensington (AU)

( * ) Notice: Subject to any disclaimer, the term of this patent is extended or adjusted under 35 U.S.C. 154(b) by 952 days.

(21) Appl. No.: 15/888,326

(22) Filed: Feb. 5, 2018

(65) Prior Publication Data

US 2018/0256900 A1    Sep. 13, 2018

Related U.S. Application Data

(62) Division of application No. 14/321,042, filed on Jul. 1, 2014, now Pat. No. 9,884,197.

(30) Foreign Application Priority Data

Jul. 1, 2013  (AU) ................................ 2013902440

(51) Int. Cl.
*A61N 1/375* (2006.01)
*A61N 1/02* (2006.01)
*H01L 23/055* (2006.01)
*H04R 25/00* (2006.01)
*H05K 3/28* (2006.01)
*A61N 1/36* (2006.01)

(52) U.S. Cl.
CPC ............ *A61N 1/375* (2013.01); *A61N 1/025* (2013.01); *H01L 23/055* (2013.01); *H04R 25/606* (2013.01); *A61N 1/36038* (2017.08); *H01L 2224/11* (2013.01); *H01L 2924/0002* (2013.01); *H04R 2460/13* (2013.01); *H05K 3/284* (2013.01); *Y10T 29/49126* (2015.01); *Y10T 29/49155* (2015.01); *Y10T 29/49156* (2015.01)

(58) Field of Classification Search
None
See application file for complete search history.

(56) References Cited

U.S. PATENT DOCUMENTS

| | | | |
|---|---|---|---|
| 5,755,743 A * | 5/1998 | Volz | A61N 1/3754 607/36 |
| 6,822,326 B2 | 11/2004 | Enquist et al. | |
| 7,190,051 B2 | 3/2007 | Mech et al. | |
| 7,904,148 B2 * | 3/2011 | Greenberg | H05K 1/028 607/2 |
| 8,393,222 B2 * | 3/2013 | Crivelli | G01L 9/0052 73/721 |
| 2008/0066524 A1 * | 3/2008 | Cummings | G01M 3/229 73/40.7 |

(Continued)

*Primary Examiner* — Daniel S Larkin
(74) *Attorney, Agent, or Firm* — Pilloff Passino & Cosenza LLP; Martin J. Cosenza

(57) ABSTRACT

A device, including an implantable electronic circuit integrated at least one of in or on a substrate, wherein the device includes a hermetic enclosure having a space therein, wherein the substrate forms at least a portion of the hermetic enclosure.

18 Claims, 23 Drawing Sheets

(56) References Cited

U.S. PATENT DOCUMENTS

| | | | |
|---|---|---|---|
| 2008/0102096 A1* | 5/2008 | Molin | B81B 7/007 |
| | | | 424/422 |
| 2010/0262208 A1* | 10/2010 | Parker | A61N 1/375 |
| | | | 156/64 |
| 2011/0137414 A1* | 6/2011 | Litzke | A61N 1/3752 |
| | | | 623/11.11 |
| 2011/0153232 A1* | 6/2011 | Ito | G01M 3/002 |
| | | | 702/51 |
| 2012/0010476 A1* | 1/2012 | Chambers | A61N 1/378 |
| | | | 600/301 |
| 2012/0247218 A1* | 10/2012 | Crivelli | G01L 9/0073 |
| | | | 73/724 |
| 2013/0100595 A1 | 4/2013 | Koester et al. | |
| 2015/0005573 A1 | 1/2015 | Lehmann et al. | |

* cited by examiner

ENCAPSULATED ELECTRONIC CIRCUIT

CROSS-REFERENCE TO RELATED APPLICATIONS

This application is a Divisional application of U.S. application Ser. No. 14/321,042, filed Jul. 1, 2014, now U.S. Pat. No. 9,884,197, naming Torsten LEHMANN as an inventor, which claims priority to Australia Application No. 2013902440, filed Jul. 1, 2013. The entire contents of each application are incorporated herein by reference in their entirety.

BACKGROUND

Medical devices having one or more implantable components, generally referred to herein as implantable medical devices, have provided a wide range of therapeutic benefits to recipients (sometimes referred to herein as patients). Included among implantable medical devices are active implantable medical devices (AIMDs), which are medical devices having one or more implantable components that rely for their functioning upon a source of power other than the human body or gravity, such as an electrical energy source. AIMDs often include an implantable electronics module, and a device that interfaces with the recipient, sometimes referred to herein as a recipient interface. The recipient interface may be a device that interfaces with a recipient's tissue, sometimes referred to as a tissue interface. The tissue interface may, for example, diagnose, monitor, and/or treat a disease or injury, modify a patient's anatomy, or modify a physiological process of a patient.

For example, an AIMD tissue interface may include one or more conductive electrical contacts, referred to as electrode contacts, which deliver electrical stimulation signals to, or receive signals from, a patient's tissue. The electrode contacts are typically disposed in a biocompatible electrically non-conductive carrier, and are electrically connected to the electronics module. The electrodes and the non-conductive member are collectively referred to herein as an electrode assembly or electrode array. Alternatively and/or in addition to this, an AIMD tissue interface can be a mechanical transducer that delivers stimulation to patient by vibrating tissue of the recipient and/or moving tissue of the recipient. As yet another example, the patient interface may include a transducer that indirectly interacts with a patient's tissue by, for example, providing signals to a patient. Also, devices that both provide electrical stimulation and mechanical stimulation can be utilized in some embodiments.

SUMMARY

In an exemplary embodiment, there is a device, comprising an implantable electronic circuit integrated at least one of in or on a substrate, wherein the device includes a hermetic enclosure having a space therein, wherein the substrate forms at least a portion of the hermetic enclosure.

In another exemplary embodiment, there is a device, comprising, an implantable housing configured to establish a hermetic volume therein, wherein the device is configured to enable hermeticity testing via active sensing of one or more phenomena in the hermetic volume.

In another exemplary embodiment, there is a method, comprising obtaining a substrate having vias extending therethrough from a first face to a second face opposite the first face, applying a first electrically conductive material onto a first face of the substrate over the vias, and inserting a second electrically conductive material into the vias, such that the second electrically conductive material extends to the second face of the substrate, wherein the second electrically conductive material is in electrical communication with the first electrically conductive material.

BRIEF DESCRIPTION OF THE DRAWINGS

Embodiments of the present invention are described below with reference to the attached drawings, in which.

DETAILED DESCRIPTION

Aspects of the present invention are generally directed to an encapsulated electronic circuit of an implantable medical device configured to operate one or more auxiliary components connectable to the encapsulated electronic circuit. The encapsulated electronic circuit comprises one or more functional components, including hardware components disposed in a housing that establishes a hermetic barrier between an interior of the housing an ambient environment of the housing. In an exemplary embodiment, these one or more functional components are part of an integrated circuit that is integrated in and/or on a substrate that forms a wall of the housing. The housing includes one or more auxiliary component interfaces disposed on the housing configured to electrically connect an auxiliary components to the hardware components inside the housing.

Figure 1:
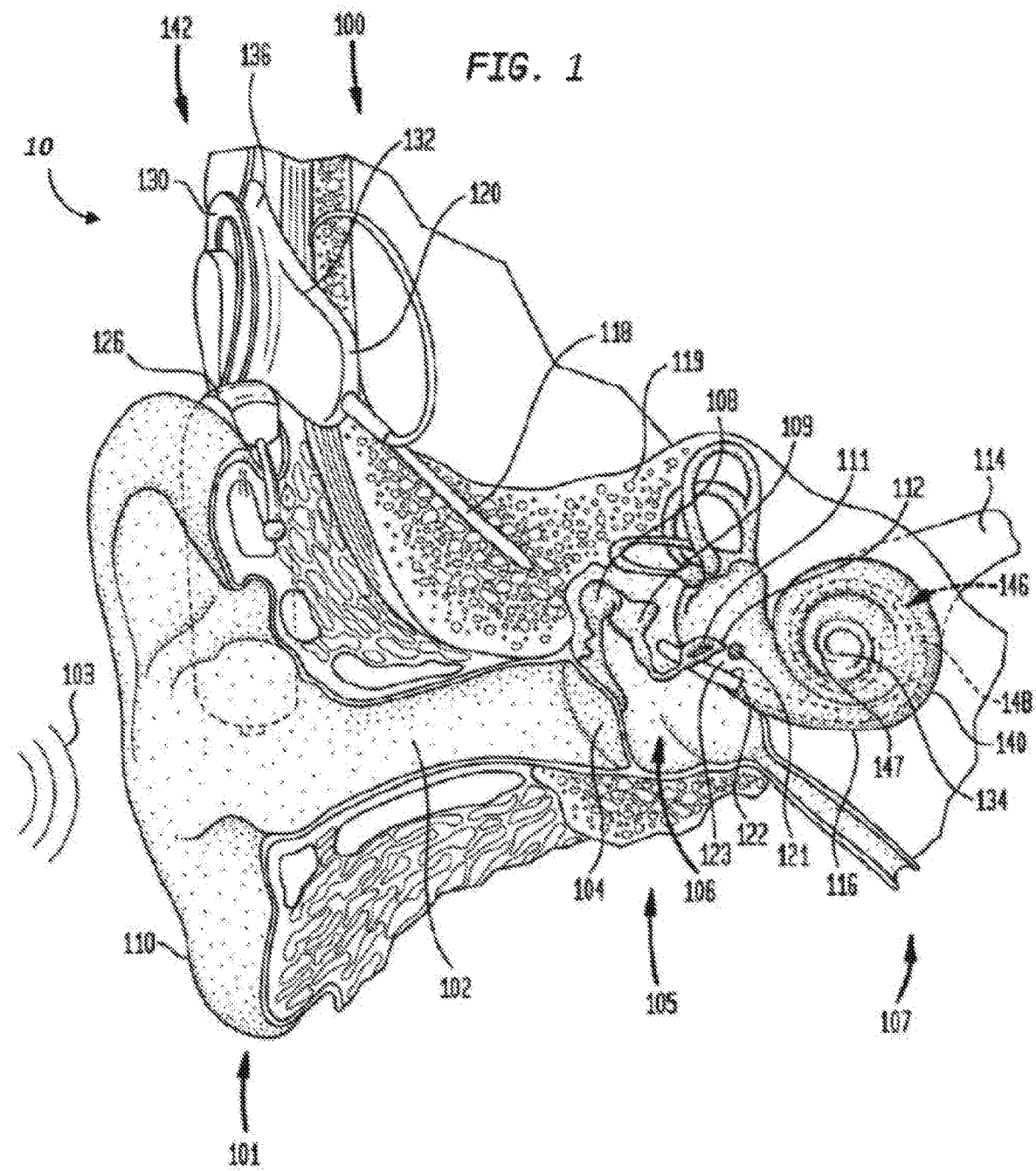
FIG. 1 illustrates one example of a conventional cochlear implant having a dedicated electronics module manufactured to operate the attached cochlear implant electrode assembly.

FIG. 1 is a is perspective view of a cochlear implant, referred to as cochlear implant 100, implanted in a recipient, to which some embodiments detailed herein and/or variations thereof are applicable. The cochlear implant 100 is part of a system 10 that can include external components, in some embodiments, as will be detailed below. It is noted that the teachings detailed herein are applicable, in at least some embodiments, to partially implantable and/or totally implantable cochlear implants (i.e., with regard to the latter, such as those having an implanted battery and/or microphone, or other type of electronic component, etc.). It is further noted that the teachings detailed herein are also applicable to other stimulating devices that utilize an electrical current beyond cochlear implants (e.g., auditory brain stimulators, pacemakers, deep brain stimulators, pain relief stimulators, vision prostheses, etc.).

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery or other energy storage device (e.g., capacitor) that is charged (e.g., recharged) by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

As noted above, cochlear implant 100 is one type of implantable hearing prosthesis to which the teachings detailed herein and/or variations thereof can be applicable. Other types of hearing prostheses include, by way of example only and not by way of limitation, bone conduction devices, middle-ear implants/Direct Acoustic Cochlear Implants, etc. Also, other types of cochlear implants can be used. For example, the array 118 can be an active electrode array and/or a device that provides electrical current and mechanical stimulation to the cochlea (or other tissue), or alternatively, just mechanical stimulation, directly and/or indirectly. An exemplary embodiment can be an electromechanical actuator (or a plurality of such) that can be located in the cochlea, where actuation of one or more actuators imparts stimulation to the cochlea tissue (e.g., by creating pressure waves in the fluid of the cochlea) to evoke a hearing percept.

Generally, each type of hearing prosthesis is manufactured with an electronics module configured specifically to operate an attached patient interface. As such, different types of implantable hearing prostheses are generally manufactured independently using separate production lines. At least some embodiments detailed herein and/or variations thereof are generally directed to an encapsulated electronic circuit corresponding to the electronics module for an implantable medical device configured to operate any of one or more components (e.g., auxiliary components) connectable to the encapsulated electronic circuit. Indeed, in at least some embodiments, the encapsulated electronic circuits according to the teachings detailed herein can be directed to an electronics module for an implantable medical device configured to operate any of one or more components connectable to the encapsulated electronic circuit.

It is further noted that while embodiments detailed herein are generally described in terms of embodiments directed towards hearing prostheses, other embodiments are directed towards other types of medical devices, such as by way of example only and not by way of limitation, pacemakers, muscle stimulators, retinal devices, etc. In at least some embodiments, the encapsulated electronic circuits detailed herein and/or variations thereof are applicable to any type of implantable medical device to which the teachings detailed herein are applicable.

Figure 2:
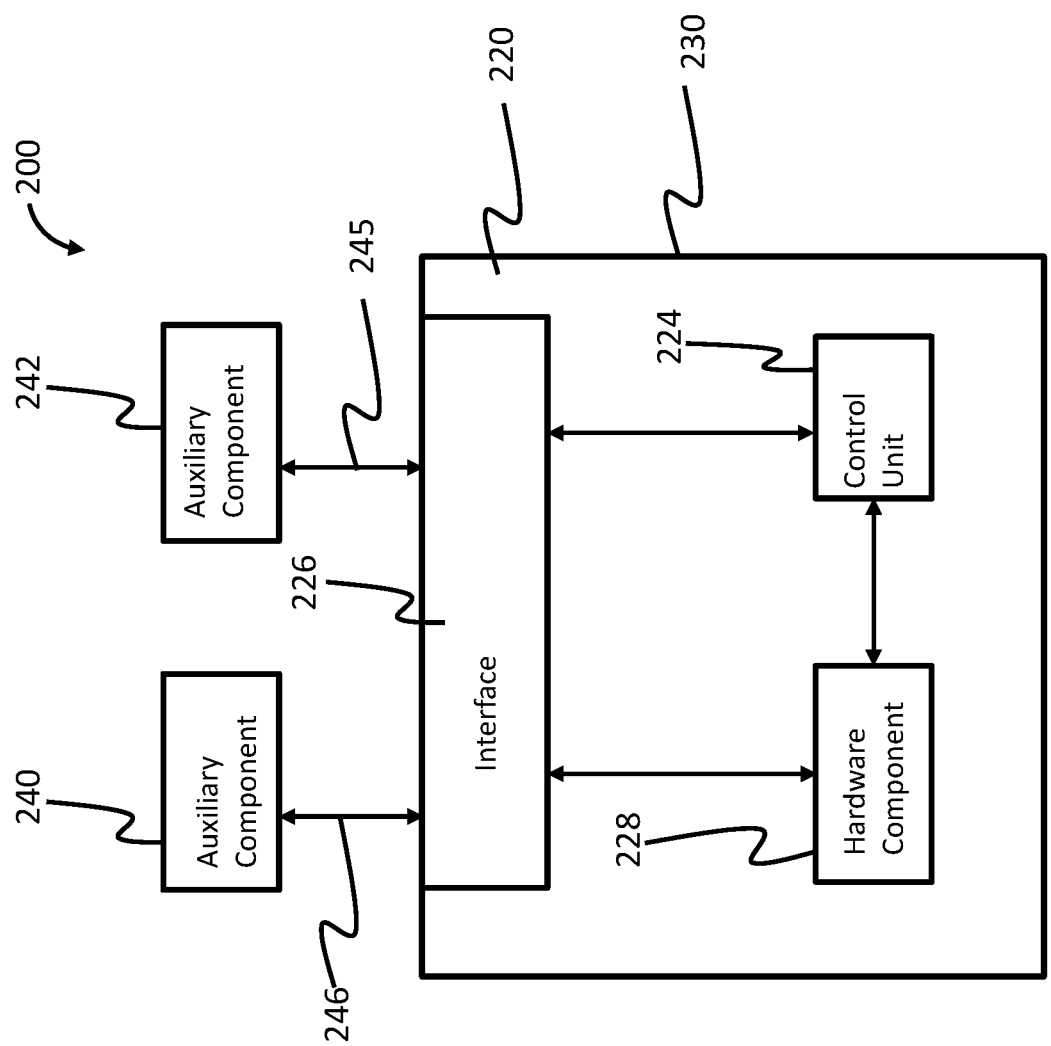
FIG. 2 is a functional block diagram of one embodiment of an implantable hearing prosthesis utilizing encapsulated electronic circuit according to the teachings detailed herein and/or variations thereof.

FIG. 2 presents an exemplary functional block diagram of one embodiment of an implantable hearing prosthesis 200 including an encapsulated electronic circuit 220, in accordance with an exemplary embodiment. As used herein, an "implantable hearing prosthesis" is a hearing prosthesis having one or more implantable components. Implantable hearing prosthesis 200 includes an encapsulated electronic circuit 220 electrically connected to auxiliary components 240 and 242. Encapsulated electronic circuit 220 includes in the exemplary embodiment depicted in FIG. 2, a housing 230, a control unit 224, functional components such as hardware components 228, and interface 226, corresponding to feedthroughs through the housing 230 (additional details of which will be described below). As used herein, a "functional component" is any component utilized to operate or drive an auxiliary component during operation of the universal implant, or any component or software utilized by those components. Control unit 224 and hardware components 228 are disposed within the confines of housing 230. In some embodiments, auxiliary component interface 226 are disposed in the surface of housing 230 such that they are accessible from outside of housing 230, as will be detailed herein. In an exemplary embodiment, encapsulated electronic circuit 220 corresponds to the main implantable component 120 of FIG. 1, where the elongate electrode assembly 118 is an auxiliary component that is connected to the encapsulated electronic circuit in such a manner that electronic communication between the elongate electrode assembly 118 and the encapsulated electronic circuit is established according the teachings detailed herein, as will be further described below.

In the embodiment illustrated in FIG. 2, encapsulated electronic circuit 220 is connected to auxiliary components 240 and 242, although in an alternate embodiment, it is connected to fewer or more auxiliary components. As shown in FIG. 2, auxiliary components 240 and 242 are electrically connected to auxiliary component interface 226 by buses 245 and 246 (the arrows of FIG. 2 indicate busses), respectively. Each of buses 245 and 246 can include one or more lines, and may include the same or a different number of lines. As used herein, an "auxiliary component" is any component that may be electrically connected to and operated by a universal implant of an AIMD. For example, an auxiliary component may be a recipient interface for any type of implantable hearing prosthesis. An example of such recipient interfaces include any type of cochlear implant electrode assembly. Other examples of a patient interface include a transducer for use with a DACI, a transducer for use with a bone conduction implant and/or any other type of transducer or other tissue interface for use as part of an implantable hearing prosthesis and/or another type of prosthesis, such as, by way of example only and not by way of limitation, a visual prosthesis (e.g., a retinal implant). In addition to recipient interfaces, an auxiliary component can be any other type of component that may supplement an AIMD. Examples of such supplementary components include input components (e.g., external or implantable microphones, telecoils, etc.), communication components (e.g., inductive coils, capacitive data transfer elements) sensors, implantable power supplies, implantable transceivers, implantable processors, etc.

As noted above, encapsulated electronic circuit 220 comprises a control unit 224, although in other embodiments, such is not present. Control unit 224 is electrically connected to auxiliary component interface 226 by a bus represented by the arrows. In an exemplary embodiment, control unit 224 is configured to identify one or more auxiliary components for operation with encapsulated electronic circuit 220, select one or more functional components for operation with encapsulated electronic circuit 220 based the identified auxiliary components, and adapt the selected functional components for operation with the identified auxiliary components. In an exemplary embodiment, control unit 224 is a control unit of the implantable component of the cochlear implant of FIG. 1, described above. By way of example, the encapsulated electronic circuit 220 can correspond to the stimulator of the cochlear implant, bus 246 can correspond to the lead extending from the stimulator to the electrode array, and auxiliary component 240 can correspond to the electrode array. Auxiliary component 242 can correspond to a telecoil implanted in the recipient, and bus 245 can correspond to the connection between the telecoil and the stimulator.

In certain embodiments, auxiliary component interface 226 may comprise a plurality of external connections to which buses 245 and 246 of auxiliary components 240 and 242 can be connected. Some additional details of some exemplary embodiments are described below, after the following description of the structure of the encapsulated electronic circuit 220.

Figure 3:
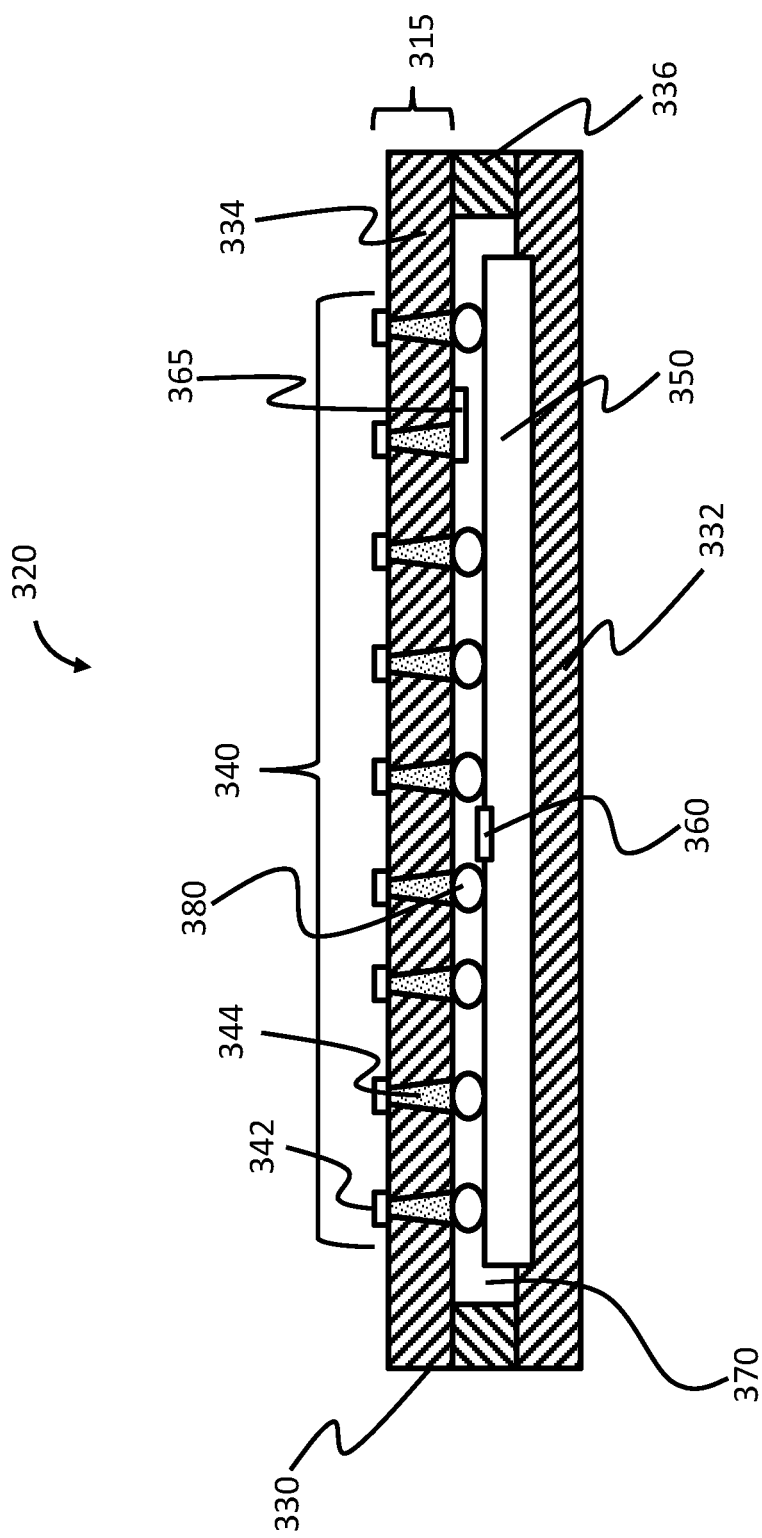
FIG. 3 is a cross-sectional view of an exemplary encapsulated electronic circuit according to an exemplary embodiment.

FIG. 3 depicts a cross-sectional diagram of an electronic apparatus in accordance with an exemplary embodiment. Specifically, FIG. 3 depicts an encapsulated electronic circuit 320, corresponding to the encapsulated electronic circuit 220 detailed above, comprising an implantable electronics circuit 350 integrated in and/or on substrate 332. The encapsulated electronic circuit 320 of FIG. 3 includes a hermetic enclosure formed by the housing 330 (corresponding to housing 220 of FIG. 2) having a space 370 therein. The substrate 332 forms at least a portion of the hermetic enclosure. The housing 330 is configured to hermetically isolate the space 370 of the hermetic enclosure and the electronic circuit 350 from an environment in a body of a recipient (e.g., from body fluids when implanted in a recipient). As can be seen, in the embodiment of FIG. 3, the substrate 332 forms a wall of the housing 330. Thus, according to an exemplary embodiment, there is no component between the electronic circuit 350 and the housing that establishes the hermetic enclosure and is directly exposed to the ambient environment (e.g., body fluid of the recipient).

In an exemplary embodiment, encapsulated electronic circuit 320 corresponds to a miniaturized implantable medical device (IMD).

FIG. 3 depicts an encapsulation component in the form of a substrate 334, hereinafter sometimes referred to as a lid 334, that forms a part of the housing 330. The lid 334 is connected to the housing by side housing portion 336, which can be a walled structure. In an exemplary embodiment, side housing portion 336 corresponds to a bonding stack that comprises several metallization layers—additional details of the bonding between the two are described below. In an exemplary embodiment, there is no side housing portion 336. Instead, substrate 332 is bonded directly to the lid 334 such as in embodiments where the lid 334 is a domed shape or otherwise includes a hollow portion sufficient to establish the space 370 of the hermetic enclosure/provide room for the integrated circuit 350 and other sensors as detailed herein.

Thus, there is an electronic apparatus, comprising an electronics circuit 350 integrated in or on (or both) substrate 332, and an encapsulation shell encapsulating the electronics circuit 350, the substrate 332 forming at least a portion of the encapsulation shell, where, in an exemplary embodiment, the encapsulation shell corresponds to the housing 330. By way of example only and not by way of limitation, in the embodiment of FIG. 3, the substrate 332 forms a base of the encapsulation shell corresponding to the housing 330.

In at least some embodiments, using the substrate 332 within which and/or on which the electronic circuit 350 is formed, to establish at least part of the encapsulation shell, can have utilitarian value in that a reduction in size (e.g., a substantial reduction in size) of the encapsulation and the electronic apparatus can be achieved, relative to that which would be the case if the electronic circuit 350 was not integrated in and/or on substrate 332. Still further, as can be seen from FIG. 3, in an embodiment, the encapsulation shell includes a portion formed by the substrate 332 and a further portion (e.g., lid 334). In the embodiment of FIG. 3, the encapsulation component (lid 334) is a shell that is of the same type of material as the substrate. In an exemplary embodiment, this can have utility in that it enables coefficient of thermal expansion matching and reduces stresses in the assembly from temperature shocks and cycles which might otherwise be the case if the components were made from different material, such as material that has different coefficient of thermal expansions. This is described in greater detail below.

In an exemplary embodiment, the electronic circuit 350 is an integrated silicone-on-sapphire (SOS) circuit. Accordingly, in an exemplary embodiment, the substrate comprises sapphire (and thus the lid 334 also comprises sapphire in embodiments where the material of the lid 334 corresponds to that of the substrate 332). Utilizing a sapphire base of the application-specific integrated circuit (ASIC) of circuit 350 (where, for example, circuit 350 is configured to perform some and/or all of the functions of the control unit 224 detailed above with respect to FIG. 2) as part of the encapsulation in this embodiment can have utilitarian value in that it can result in significant reduction in size of the apparatus, at least relative to that which would be the case without utilizing such features.

While the embodiments detailed herein are described in terms of utilization of sapphire as substrate(s) and in terms of the integrated circuits detailed herein being integrated SOS circuits, alternate embodiments can utilize other types of arrangements. By way of example only and not by way of limitation, ceramic substrates can be utilized in some alternate embodiments, and thus silicone-on-ceramic circuits can be used in at least some embodiments. Other types of organic substrates (e.g., substrates made of plastics) can be utilized in at least some embodiments. Any composition of substrate that can enable ASIC or other types of circuits to be integrated in and/or on that substrate that can enable the teachings detailed herein and/or variations thereof to be practiced can utilize in at least some embodiments.

Figure 4:
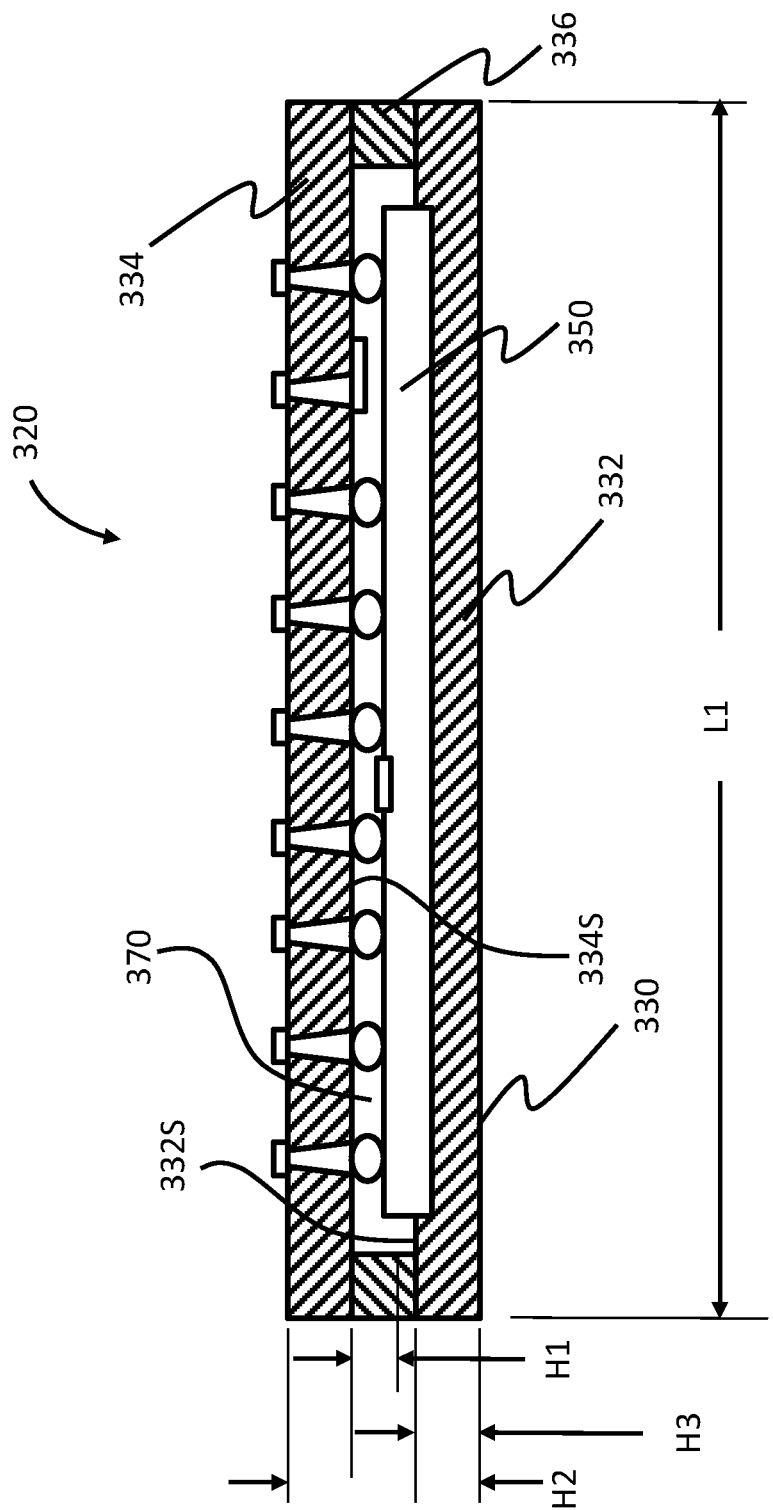
FIG. 4 is also a cross-sectional view duplicate of a vat of FIG. 3, except presenting additional reference numerals and legends for ease of identification.

With reference to FIG. 4, it can be seen that the encapsulation component (lid 334) of the encapsulated electronic circuit 320 includes at least a portion that is spaced away from the substrate 333/spaced away from the ASIC 350 a distance H1 (a leader line for H1 is depicted in between the top of the substrate 332 and the top of the ASIC 350 to indicate that the values for H1 can be for the distance between the substrate 332 and the substrate 334 or for the ASIC 350 and the substrate 334). The encapsulation component (substrate 334) and the substrate 332 form at least a portion of the hermetic enclosure (the side housing component 336 forming the rest of the hermetic enclosure, if present, the encapsulation component 334 and the substrate 332 forming the entire hermetic enclosure in alternate embodiments). The space 370 in the hermetic enclosure is established at least in part by the spacing away of the encapsulation component (substrate 334) from the substrate 332.

In an exemplary embodiment, the space 370 is an "air-gap" (where "air-gap" does not require that the gap actually include air-any gas and/or a vacuum and/or any fluid, including liquids, that can enable the teachings detailed herein and/or variations thereof can be located in the air-gap) between a surface of the substrate 332S (which can include the surface of the ASIC 350) and a surface 334S of an adjacent wall (e.g., lid 334 of the housing 330). The height H1 of the air-gap (the distance between the surface of the substrate and the surface of the adjacent wall of the housing) as measured normal to a span-wise direction (the direction parallel to the dimension L1) of the substrate (the horizontal direction of the frame of reference of FIG. 4) and through the air-gap is no more than about 10, 15, 20, 25, 30, 35, 40, 45, 50, 55, 60, 65, 70, 75, 80, 85, 90, 95, 100, 110, 120, 130 140, 150, 175, 200, 225, 250, 275, 300, 325, 350, 375, 400, 425, 450, 475 or 500 microns or any value or range of values therebetween in about 1 micron increments (e.g., about 70 microns, about 339 microns, about 100 to about 225 microns, etc.). In an exemplary embodiment, the space can be less than about 10 microns or more than about 500 microns. Any value of H1 can enable the teachings detailed herein and or variations thereof to be practiced can utilize in at least some embodiments.

In an exemplary embodiment, the height H2 of the housing 330 as measured normal to a span-wise direction of the substrate and through the air-gap is no more than about 200, 250, 300, 350, 400, 450, 500, 550, 600, 650, 700, 750, 800, 850, 900, 950, 1000, 1050, 1100, 1150, 1200, 1250, 1300, 1350 or 1400 microns or any value or range of values therebetween in about 5 micron increments (e.g., about 465 microns, about 620 microns, about 310 to about 885 microns, etc.). Any value of H2 can enable the teachings detailed herein and or variations thereof to be practiced can utilize in at least some embodiments.

In an exemplary embodiment, the length L1 of the housing 330 is no more than about 3 mm, 4 mm, 5 mm, 6 mm, 7 mm, 8 mm, 9 mm, 10 mm, 11 mm, 12 mm, 13 mm, 14 mm or 15 mm or any value or range of values therebetween in about a tenth of a millimeter. Any value of L1 that can enable the teachings detailed herein or variations thereof to be practiced can utilize in at least some embodiments.

Figure 5:
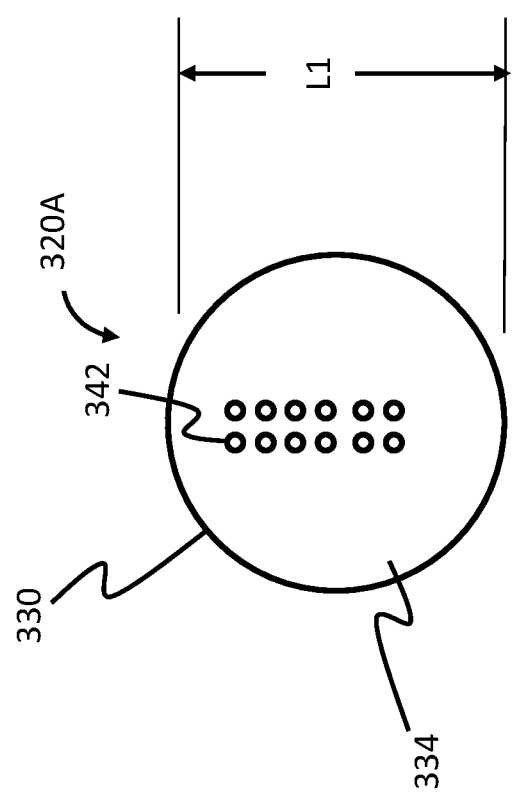
FIG. 5 is a top view of an exemplary embodiment of an exemplary encapsulated electronic circuit according to the embodiment of FIG. 3.
Figure 6:
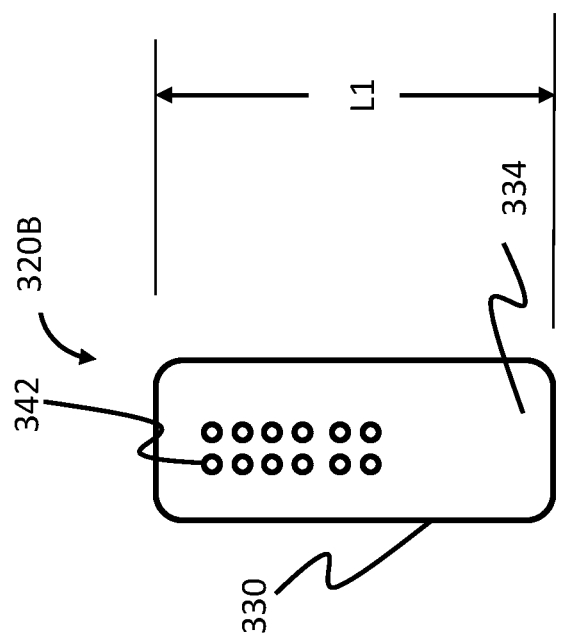
FIG. 6 is a top view of an alternate exemplary embodiment of an exemplary encapsulated electronic circuit according to the embodiment of FIG. 3.

It is noted that in at least some embodiments, the encapsulated electronic circuit 320 of the embodiments depicted in FIGS. 3 and 4 has a curved outer profile (circle or oval shaped or otherwise). FIG. 5 depicts a view of an exemplary embodiment of an encapsulated electronic circuit 320A corresponding to that of encapsulated electronic circuit 320 as viewed from above with respect to the frame of reference of FIGS. 3 and 4, where the spanwise direction is a direction normal to the longitudinal axis thereof (the axis extending out of the page of FIG. 5/the axis of rotation of the encapsulated electronic circuit 320A). That said, other embodiments can have other configurations. In this regard, the encapsulated electronic circuit 320 of the embodiments depicted in FIGS. 3 and 4 have a rectangular outer profile (square or non-square). FIG. 6 depicts a view of an exemplary embodiment of an electronics circuit 320B corresponding to that of encapsulated electronic circuit 320 as viewed from above with respect to the frame of reference of FIGS. 3 and 4, where the spanwise direction is a direction normal to the length L1 (or the width, which is normal to the length L1, and can equal L1 in some embodiments).

Again with reference to FIGS. 3 and 4, it is noted that in an exemplary embodiment, a height H2 of the housing 330 as measured normal to the span-wise direction of the substrate 332 and through the space 370 is no more than about one, two, three, four, five, six, seven, eight, nine, ten, eleven, twelve, thirteen fourteen or fifteen times, or any value or range of values therebetween in about a tenth of an increment, of a thickness H3 of the substrate 332, also measured normal to the span-wise direction. In this regard, it is noted that in an exemplary embodiment, H3 can be about equal to H1. That said, in an alternate embodiment, H3 can be different from H1. The height H3 can be, in some embodiments, no more than about 25, 50, 75, 100, 125, 150, 175, 200, 225, 250, 275, 300, 325, 350, 375, 400, 425, 450, 475, 500, 525, 550, 575, 600, 625, 650, 675, 700, 725 or 750 microns or any value or range of values therebetween in about 1 micron increments (e.g., about 150 microns, about 316 microns, about 300 to about 369 microns, etc.).

It is further noted that in an exemplary embodiment, the volume of space 370 corresponds to a value that is about $1/10$, $2/10$, $3/10$, $4/10$, $5/10$, $6/10$, $7/10$, $8/10$, $9/10$, one, two, three, four or five times, or any value or range of values therebetween in about one twenty-fifth of an increment, of a volume of the substrate 332.

It is noted that any use of the term "about" also corresponds to a disclosure of the exact value as well, unless otherwise noted.

It is noted that in an exemplary embodiment, an SOS ASIC passivation overglass of SiO2 or any other compatible material is present over the circuit 350 and, in some embodiments, over the entire substrate 332 save for the edges that interface with the side housing component 336. That is, in an exemplary embodiment, the overglass is not present at the edges of the substrate 332, allowing bonding of the sapphire lid encapsulation and/or the housing component 336 to the ASIC sapphire substrate 332. In an exemplary embodiment, the over glasses removed from the edges to enhance or otherwise unable the connection of the substrate 332 with the substrate 334. Additional details of this will be described below with respect to an exemplary manufacturing process.

Again with reference to FIGS. 3 and 4, it is noted that an exemplary embodiment includes a hermetically sealed feedthrough 340, corresponding to interface 226 of the embodiment of FIG. 2, that is integral to the substrate 334. In an exemplary embodiment, feedthrough 340 in the substrate 334 allows for external connections between the internal components (e.g., hardware 228 and/or controller 224) and the auxiliary functional components 240 and 242 (e.g., a cochlear electrode array, an actuator of an active transcutaneous bone conduction device, etc., or any other utilitarian functional component that can function in conjunction with the encapsulated electronic circuit 320 (e.g., a direct galvanic communication and power transfer to the implant ASIC, or as will be detailed further below, a connection to the integrated hermeticity sensor)).

More particularly, feedthrough 340 includes external connection components 342 made of a first electrically conductive material (e.g., silver, as will be detailed below) that is located on a face of the lid 332 (which can correspond to a second substrate, as will also be detailed below). In an exemplary embodiment, these external connection components 342 are spaced apart from one another so as to avoid a short-circuit or the like, and are configured to interface with a mating component that mates or otherwise connects to the encapsulated electronic circuit to establish an electrical connection between these external connection components 342 and a mating connector of a bus (e.g., one of busses 246 or 245) that leads to the pertinent auxiliary functional component. (An exemplary mating arrangement is described below.)

These external connection components 342 are located over vias that extend through the lid 334, from an interior location to an exterior location relative to the space 370 inside the housing 330. In an exemplary embodiment, electrically conductive pins 344 which fill the vias extend from an interior location to respective external connection component 342. The electrically conductive pins 344 place the interior of the encapsulated electronic circuit 320 into electrical communication with the external connection components 342, and thus the exterior of the encapsulated electronic circuit 320. In an exemplary embodiment, the pins 344 are made of a second electrically conductive material (e.g., platinum) that is different from the first electrically conductive material of the external connection component 342. That said, in an alternate embodiment, the materials can be the same. In this regard, it is noted that any type of material that can enable the teachings detailed herein and/or variations thereof, that is electrically conductive, and that can be utilized to establish feedthrough 340, can be utilized in at least some embodiments.

Stud bumps 380 (sometimes referred to as ball bonds) establish electrical connections between the pins 344, and thus the feedthrough 340, and corresponding bonding areas ASIC 350. That said, in an alternate embodiment, another configuration can be utilized to place the pins 344 into electrical communication with the ASIC 350. Indeed, in an exemplary embodiment, the pins can be such that the pins are proud of the interior surface 334S of the lid 334, extending to mating components of the ASIC 350. Any device, system and/or method that can enable the ASIC 350 to be placed into electrical communication with the feedthrough 340 can be utilized in at least some embodiments.

As noted above, the feedthrough 340 is a hermetically sealed feedthrough. In this regard, the configuration of the pins 344 which can fill the vias and/or the external connection components 342, which can completely cover the vias, alone and/or in combination, can establish the hermeticity of the feedthrough 340 vis-à-vis substrate 334. That said, in an alternate embodiment, an arrangement on the interior of the substrate 334 can be utilized to establish the hermeticity of the feedthrough 340. Any device, system and/or method of establishing a hermetic feedthrough through the housing 330 can be utilized in at least some embodiments.

As noted above, an exemplary embodiment of the encapsulated electronic circuit 320 includes an implantable housing 330 that is configured to establish a hermetic volume therein (e.g., that of space 370). In an exemplary embodiment of such an exemplary embodiment, the encapsulated electronic circuit 320 is configured to enable hermeticity testing via active sensing of one or more phenomena in the hermetic volume. Additional details of such exemplary embodiments will now be described, but first it is noted that the teachings detailed herein associated with hermeticity testing can be practiced utilizing other devices that those detailed herein (e.g., a non-encapsulated electronic circuit). That is, by way of example only and not by way of limitation, in at least some embodiments, the teachings detailed herein associated with hermeticity testing can be applicable to any housing that establishes a hermetic volume therein, regardless of whether it encapsulates an electronics circuit and/or regardless of whether it utilizes the SOS ASIC or equivalent teachings.

Again with reference to FIGS. 3 and 4. The exemplary encapsulated electronic circuit 320 includes two arrangements that can be utilized for hermeticity testing, one for in-situ testing after implantation, and another for laboratory/manufacturing testing (e.g., quality control), as will now be detailed by way of example. It is noted that in some exemplary embodiments, only one of these arrangements is utilized with the exemplary encapsulated electronic circuit 320.

With respect to the laboratory/manufacturing testing embodiment, as noted above, embodiments of the encapsulated electronic circuits according to the teachings detailed herein and/or variations thereof can have an internal volume (space 370) that is relatively small, at least as compared to other implantable medical devices. As noted above, some exemplary embodiments can have an internal volume that is about the same as or less than about two times the volume of the substrate 332. By way of example only and not by way of limitation, an exemplary embodiment can have an internal hermetically sealed volume (space 370) in the housing 330 corresponding to about 50, 40, 30, 29, 28, 27, 26, 25, 24, 23, 22, 21, 20, 19, 18, 17, 16, 15, 14, 13, 12, 11, 10, 9, 8, 7, 6, 5, 4, 3 or 2 mm3 or less or any value or range of values therebetween in about 0.1 mm3 increments. Such limited volumes can frustrate the ability to utilize helium testing, where the interior volume is filled with helium, and a leak test is performed utilizing the sensor located on the outside of the housing to determine whether or not helium leaks therefrom. In this regard, the amount of helium would be minimal, and thus if there is indeed a breach in the hermetic volume (e.g., the volume is instead an almost-hermetic volume), the amount of helium that would leak therefrom is not detectable in a manner that provides utilitarian hermeticity testing.

Accordingly, an exemplary embodiment includes a method where the housing 330 is placed into an environment where there is hydrogen (with relatively little to no hydrogen in the volume 370—that is, the volume is effectively devoid of hydrogen and/or any hydrogen within the volume 370 is undetectable by the sensors according to the embodiments detailed herein), and internal sensing is performed to determine whether hydrogen is detected inside the volume 370. If the housing establishes a hermetic volume (i.e. there are no breaches/the housing is properly sealed), the sensors will not detect any hydrogen intrusion into the volume. Conversely if the housing merely establishes an almost-hermetic volume (i.e., there is a breach in the housing/the housing is not properly sealed, but, for example, for all intents and purposes, the volume should be hermetically sealed), hydrogen will leak into the volume, and the sensors according to the teachings detailed herein will detect the hydrogen, and thus indicate that the volume is not hermetically sealed. It is noted that while hydrogen gas is utilized in the embodiments detailed herein, in alternate embodiments other types of gases can be utilized. Indeed in an alternate embodiment other types of liquid can be utilized. Any fluid that can enable the teachings detailed herein and or variations thereof to be practiced can utilize in at least some embodiments.

Additional details of some exemplary methods of testing for hermeticity will be described below, but first, some exemplary sensing apparatuses will now be described.

The exemplary encapsulated electronic circuit 320 of FIG. 3 is configured to actively sense hydrogen intrusion into an almost-hermetic volume corresponding in size to any of the volumes noted herein and/or variations thereof. In an exemplary embodiment, the encapsulated electronic circuit 320 includes one or more hermeticity sensor components at least one of internal or integral to the housing, wherein the hermeticity sensor component is configured to enable active sensation of the one or more phenomena, thereby enabling the hermeticity testing. Sensor component 365 will first be discussed, followed by sensor 360.

In an exemplary embodiment, sensor component 365 corresponds to an apparatus that is exposed to the hermetic volume 370. The apparatus can be, in an exemplary embodiment, a wire, such as by way of example only and not by way of limitation, a palladium wire (e.g., a palladium nano-wire), having a structure such that the electrical capacitance and/or electrical resistance thereof changes or otherwise is detectably different in the presence of hydrogen in the volume. This enables the sensor component 365, when used in conjunction with other components, to be used as a hydrogen sensor.

Thus, the hermeticity sensor component 365 enables the evaluation of a physical phenomenon associated with at least one of capacitance or resistance of a structure (the wire) exposed to the volume 370, and enables an output of a signal indicative of a change in the physical phenomenon, thereby indicating a change in a status of hermeticicy of the volume. More particularly, the apparatus of the sensor component (e.g., palladium wire) is in electrical communication with an exterior of the volume 370/housing 330. By way of example only and not by way of limitation, this is accomplished via pins 344 and external connection components 342. Thus, in an exemplary embodiment, the encapsulated electronic circuit 320 (or other applicable implantable device) can include one or more electrical interfaces integral with the housing 330 (pins 344), where the one or more electrical interfaces correspond to a location on the housing exposed to an ambient environment. Accordingly, the sensor component (palladium wire) is in electrical communication with the location of the housing 330 exposed to ambient environmental the housing. In this regard, by way of example only and not by way of limitation, one end of the wire of sensor component 365 can be connected to one of the pins 344, and another end of the wire of the sensor component 365 can be connected to another of the pins 344. This can be duplicated or triplicated or more to provide redundancy in at least some embodiments.

An electrical circuit can be established via the external connection components 342 that extends through the wire. This can be accomplished by placing a connector onto the top of the lid 334, that connects the pertinent external connection components to a device that is configured to evaluate the current directed through the wire and ascertain a capacitance and/or resistance of the wire, or at least evaluate a physical phenomenon associated with the current and determine, or at least extrapolate, a capacitance and/or resistance of the wire (or at least changes thereof), and thus determine whether hydrogen has entered the volume 370 (thus indicating that the volume 370 is not a hermetic volume, but instead at most an almost-hermetic volume, and thus should not be implanted in a recipient). An exemplary connector can correspond to one of the connectors/busses detailed in the exemplary embodiment described below for placing an auxiliary component into electrical connection with the interior of the housing 330.

Accordingly, the actual sensing of the changing capacitance/resistance is performed outside the housing 330, but it is based on a change in a physical characteristic of the wire that is part of the sensor component 365 that is located inside the housing/inside the volume 370. Such an exemplary embodiment can be utilized during manufacturing testing/quality assurances, prior to implantation of the encapsulated electronic circuit 320 into a recipient, by, for example, placing the encapsulated electronic circuit 320 into a hydrogen atmosphere, as further detailed below.

In an alternate embodiment, a sensor component is integrated on the ASIC 350, and can enable in-situ hermeticitiy testing. That is, in contrast to the exemplary embodiment detailed above with respect to component 365, which was described above as an arrangement for production testing of hermeticity, where the sensor component 365 is not integrated onto an ASIC (but can be so integrated, in alternate embodiments, where electrical communication with the sensor component 365 can be established through the ASIC via the stud bumps and the pins as detailed above—that said, in alternate embodiment, the sensor component 365 can be in electrical communication with the ASIC but still not integrated there with), an exemplary embodiment includes a sensor component, such as a sensor component that is part of sensor 360, that is integral with the ASIC. However, it is noted that in alternate embodiments, the sensor component need not be integral with the ASIC (but remaining components of the sensor can be integral therewith).

More specifically, sensor 360 can be utilized for sensing in a deployed encapsulated electronic circuit 320 (e.g., implanted in the recipient). In an exemplary embodiment, at least some of the sensor components of the sensor 360 are integral/integrated into the ASIC 350. In an exemplary embodiment, all components of the sensor 360 are integrated into the ASIC 350, while in another exemplary embodiment all components except the component that reacts to the change in a physical phenomenon inside the volume 370 indicative of a failure of a hermetically enclosed volume (as will be described below) are integrated into the ASIC. Any device, system, and/or method that can enable hermeticity sensing/testing in-situ can be utilized in at least some embodiments.

With regard to an embodiment where at least a portion of the sensor 360 is integrated into the ASIC, there is thus an encapsulated electronic circuit 320 that includes a housing 330, where a wall of the housing 330 includes an electronic circuit 350 integrated therein that includes a hermeticity sensor 360. At least a part of the hermeticity sensor 360 is an integrated part of the electronic circuit. Thus, the hermeticity sensor 360 includes a sensor component that is an integrated part of the ASIC 350. The hermeticity sensor 360 can also include a sensor component that is not integrated part of the ASIC 350 (e.g. the component that reacts to a change in the physical phenomenon inside the volume indicative of a failure of the hermetic volume). However, in alternate embodiments, all components are so integrated. Accordingly, an exemplary embodiment includes an encapsulated electronic circuit 320 that includes a substrate 332 at least one of in which or on which is located an interdigitized exposed pattern corresponding to a structure exposed to the volume 370, the structure being one that has a physical phenomenon associated therewith that changes and/or occurs as a result of a failure of the hermeticity of the volume. In an exemplary embodiment, this physical phenomenon can be a change in electrical capacitance and/or electrical resistance. Any change in physical phenomenon that is indicative of a failure of the hermetic volume can utilize in at least some embodiments.

By way of example only and not by way of limitation, the sensor 360 can be configured such that it reacts to a change in the level of water molecules/humidity in the volume 370. By way of example only and not by way limitation, in at least some exemplary embodiments, failure of the hermetic volume when the encapsulated electronic circuit 320 is implanted in a recipient should result in an increase in the humidity level of the volume 370 relative to that which would be the case in a non-failure scenario. In an exemplary embodiment, a change in electrical capacitance and/or electrical resistance of the structure exposed to the volume 370 should result. In an exemplary embodiment, the sensor 360 is configured to detect such change (directly and/or indirectly), and thus provide an indication of a hermeticity failure. In an exemplary embodiment, and interdigitized exposed pattern manufactured with high digit pitch (for utilitarian sensitivity) is located on the top portion (portion closest to the lid 334) of the ASIC 350. The sensor can be a humidity sensor. The sensor 360 is configured to detect moisture ingress (leaks) by measuring (or otherwise evaluating) electrical capacitance and/or electrical resistance of the structure, or otherwise the capacitance of the structure.

In an exemplary embodiment, nano-porous hydrophilic dielectric can be used in the interdigitized sensor. In an exemplary embodiment, an optical sensor can be utilized. Any device, system and/or method, that can enable the teachings detailed herein and or variations thereof to be practiced with respect to hermeticity testing can be utilized in at least some embodiments. Accordingly, any device, system and/or method that can enable a detection of an increase or otherwise detection of a change in the humidity inside volume 370 and/or an increase and/or change in a quantity of water molecules inside volume 370 can utilize in at least some embodiments.

Accordingly, in view of the above, an exemplary embodiment includes an electronic circuit 350 encapsulated within an encapsulation shell (e.g., a shell established by housing 330), and a hermeticity sensor mounted within the encapsulation shell. In an embodiment, leak tests (hermeticitiy testing) can be applied to the encapsulation shell by detecting leaks from the outside of the encapsulation shell to the inside of the encapsulation shell, using the internally mounted hermeticity sensor component. In embodiments that utilize the feedthrough 340 to establish electrical communication with a component that reacts to an environment indicative of a failed hermetic seal, such testing can be accomplished what a device that includes a relatively small internal chamber (volume 370), which would otherwise be too small for a conventional leak test corresponding to filling the volume with a gas or a fluid and attempting to identify whether the gas or fluid has leaked out of the volume. In view of the above, some exemplary embodiments include an internal hermeticity sensor that enables in-situ monitoring of hermeticity of a device (e.g., encapsulated electronic circuit 320) during use thereof implanted in a recipient. In an embodiment, the electronic circuit is an integrated circuit integrated in or on the substrate and the hermeticity sensor is not integrated with the electronic circuit substrate. In an embodiment, the electronic circuit is an integrated circuit integrated in or on a substrate, and the hermeticity sensor is integrated with the substrate.

It is noted that while the hermeticity sensor component 365 is presented in the figures as being placed on the lid (substrate 334) and the hermeticity sensor 360 is depicted as being placed on/part of the ASIC 350, in alternate embodiments, this arrangement can be reversed. Further, in an alternate embodiment, both can be located on the ASIC and/or on the substrate 332, or alternatively, both can be located on the lid. Further, duplicate devices can be utilized and be located at any location that can enable the teachings detailed herein to be practiced.

Figure 7:
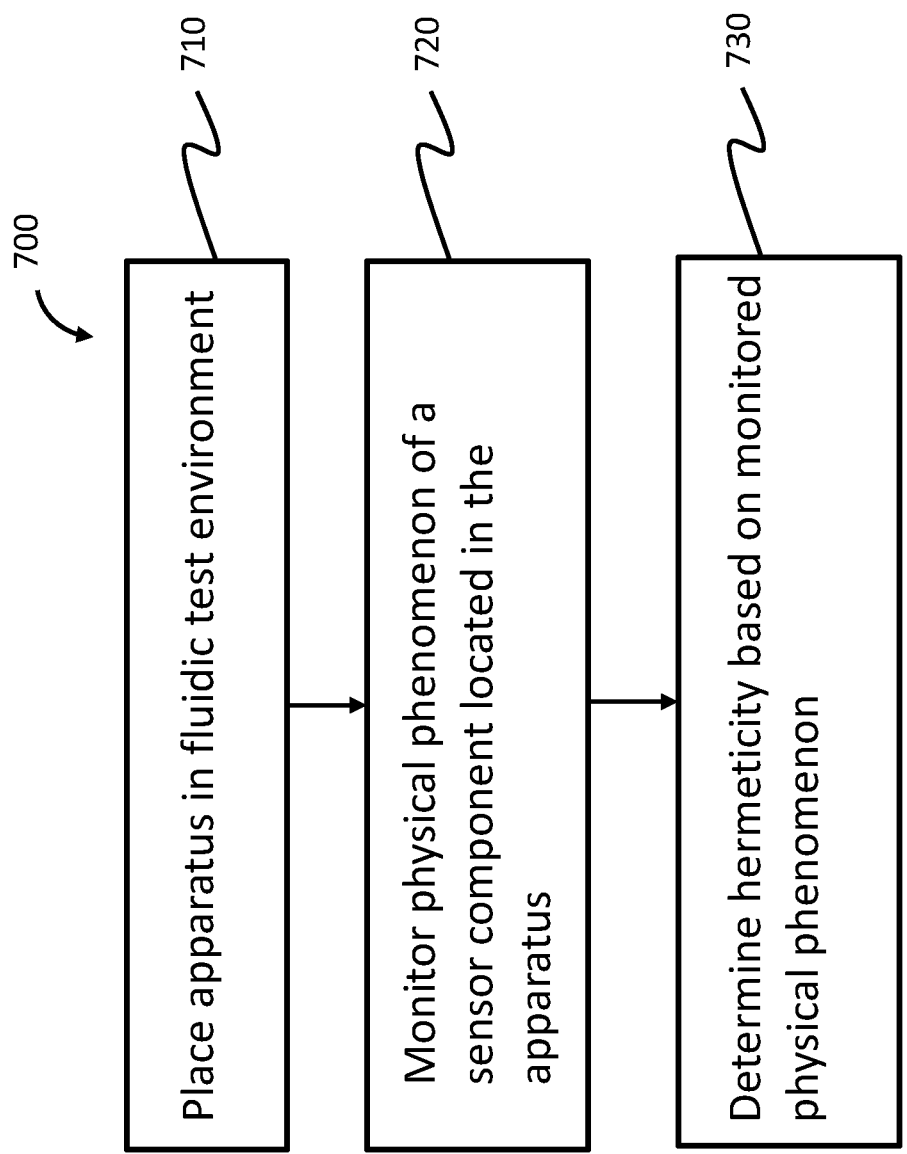
FIG. 7 is an exemplary flow chart for an exemplary method.

In view of the above, some exemplary methods of testing for hermeticity will now be described. FIG. 7 presents an exemplary flowchart for an exemplary method 700 according to an exemplary embodiment of testing for hermeticity. Method 700 includes method action 710 which entails placing an apparatus, such as by way of example only and not by way of limitation, the encapsulated electronic circuit 320 or another apparatus having a hermetic volume, into a fluid test environment configured for hermeticity testing. By way of example only and not by way of limitation, the fluidic environment can be hydrogen environment (e.g., a hydrogen gas environment). More particularly, the apparatus can be placed into a chamber configured to be pressurized (although in alternate embodiments, the chamber is not pressurized, at least not over-pressured relative to local atmospheric pressure). The chamber can be at least partially filled with a fluid that has utilitarian value with respect to hermeticity testing (e.g. hydrogen gas). The chamber can be pressurized such that the pressure in the chamber is higher than the pressure of the hermetic volume of the apparatus. Method 700 further includes method action 720, which entails monitoring the physical phenomenon of a sensor component (e.g. sensor component 365) located in the apparatus. In an exemplary embodiment, in accordance with the teachings above, a nano wire located inside the apparatus is placed into electrical communication with a device that is configured to evaluate a physical phenomenon associated with that nano wire (e.g. a changing electrical capacitance and/or electrical resistance, etc.). The device evaluates the physical phenomenon associated with that nano wire during the test. Method 700 further includes method action 730, which entails determining hermeticity based on the monitored physical phenomenon. For example, if the physical phenomenon changes during the test, at least to a certain degree, it can be determined that the fluid in the chamber (e.g., hydrogen) has entered the apparatus, and thus the apparatus is not hermetically sealed (e.g., the apparatus has an almost-hermetic volume). Thus, a determination is made that the apparatus is not hermetically sealed. Conversely, for example, if the physical phenomenon does not change, or at least does not change within a certain degree, it is determined that the fluid in the chamber has not entered the apparatus, and thus the apparatus is hermetically sealed.

Again, it is noted that method 700 can be practiced utilizing a pressurized chamber and/or an un-pressurized chamber.

From the FIG. 7, it can be seen that in an exemplary embodiment, there is a method for hermeticity testing of an electronic apparatus encapsulated within an encapsulation shell, comprising testing for ingress of a fluid into a volume formed within the shell. Method 700 can have utilitarian value with respect to testing a device during the production of electronic apparatus (e.g., as part of a quality testing regime, etc.). Method 700 can further have utilitarian value with respect to testing a device that has a relatively small internal hermetically sealed volume, such as the volumes detailed herein and/or variations thereof. Accordingly, in an alternate embodiment of method 700, the apparatus placed fluidic environment via the execution of method action 710 is an apparatus having a volume corresponding in size to any of the volumes detailed herein. Further, an exemplary embodiment includes performing a hermeticity test on an implantable component without placing the testing fluid inside the implantable component, or at least inside the hermetic volume of the implantable component.

It is noted that in the exemplary embodiment associated with method 700, other types of sensing components can be utilized other than a nano wire the like. Indeed, in an exemplary embodiment, a method of testing for hermeticity in a quality assurance environment can follow a different method. Any device, system, and/or method that can enable hermeticity testing without having to place a liquid inside an enclosed volume believed to be a hermetic volume can be utilized in at least some embodiments. Accordingly, the sensor component 365 can be different than a nano wire (e.g., it can be an optical component, etc.). Still further, while embodiments of the quality assurance testing have been disclosed with respect to communicating a signal through the housing to a device that analyzes the signal to evaluate hermeticity, in an alternate embodiment, and internal device can be utilized to evaluate hermeticity, or at least evaluate the signal and indicate values associated with a change in phenomenon (as opposed to utilizing a raw electrical signal as described above).

Figure 8:
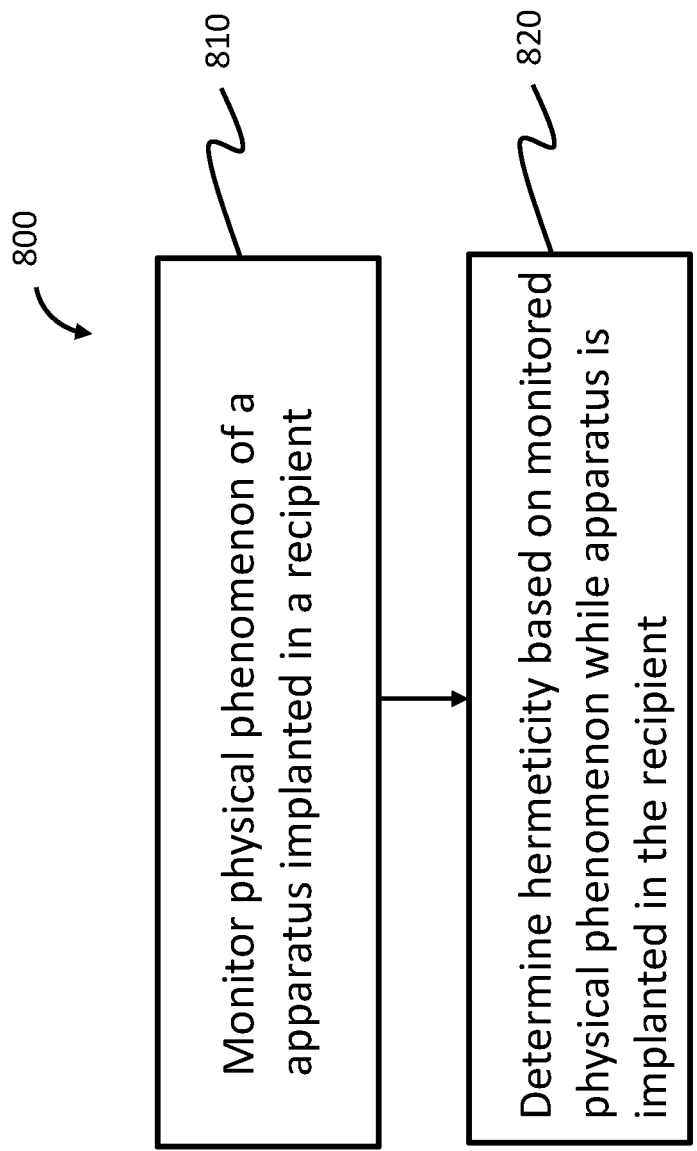
FIG. 8 is another exemplary flow chart for an exemplary method.

FIG. 8 presents an exemplary flowchart for an exemplary method 800 according to an exemplary embodiment of testing for hermeticity in an apparatus implanted in a recipient (in-situ testing). Method 800 includes method action 810 which entails monitoring (e.g., automatically monitoring) a physical phenomenon of an apparatus implanted in a recipient (e.g., encapsulated electronic circuit 320 implanted in a recipient or another component having a hermetically sealed volume implanted in a recipient, etc.). In an exemplary embodiment, the physical phenomenon is the humidity of a (desirably) hermetically sealed volume of the apparatus and/or a quantity of water molecules inside the (desirably) hermetically sealed volume. It is noted that it is not necessary to determine the humidity value/quantity value to execute method action 810. In at least some embodiments, all that is done is to obtain information indicative of the physical phenomenon (e.g., humidity) or information indicative of a change in the physical phenomenon (e.g., information indicative of a (change in) electrical capacitance and/or electrical resistance etc). Any physical phenomenon that can be monitored that can enable hermeticity testing can be utilized according to some exemplary methods. Any data that is indicative of the physical phenomenon that can be utilized to monitor the physical phenomenon can be utilized in at least some embodiments.

Method 800 further includes method action 820 which entails determining hermeticity based on the monitored physical phenomenon while the apparatus is implanted in the recipient. In an exemplary embodiment, this is executed automatically by the sensor 360 that is by way of example only and not by way of limitation, integrated into the ASIC 350. For example, if the physical phenomenon changes during the monitoring, at least to a certain degree, it is determined that the physical phenomenon has changed such that the hermeticity of the volume has been compromised, and thus the apparatus is not hermetically sealed (e.g., the apparatus has an almost-hermetic volume). Thus, a determination is made that the apparatus is not hermetically sealed. Conversely, for example, if the physical phenomenon does not change, or at least does not change within a certain degree, it is determined that the hermeticity of the volume has not been compromised, and thus the apparatus is hermetically sealed.

From FIG. 8, it can be seen that in an exemplary embodiment, there is a method for hermeticity testing of an electronic apparatus encapsulated within an encapsulation shell, comprising testing for ingress of water molecules into a volume formed within the shell. Method 800 can have utilitarian value with respect to testing a device while implanted in a recipient. Method 800 can further have utilitarian value with respect to testing a device that has a relatively small internal hermetically sealed volume, such as the volumes detailed herein and/or variations thereof. Accordingly, in an alternate embodiment of method 800, the physical phenomena monitored in method 800 is a physical phenomenon in a volume corresponding in size to any of the volumes detailed herein.

In an exemplary embodiment, the method 800 entails testing for fluid ingress. It is noted that while the above method has been described in terms of a physical phenomenon corresponding humidity (e.g., water vapor), an alternative embodiment entails a physical phenomenon corresponding to liquid fluid (e.g. water) entering the volume of the encapsulated electronic circuit 320.

It is noted that method 700 can be executed utilizing the sensor component 365 of the encapsulated electronic circuit 320, and method 800 can be executed utilizing the sensor 360, both of these being apparatuses that are mounted internal of an encapsulation shell of a implantable device.

Some exemplary methods of manufacturing at least some of the components of the encapsulated electronic circuit 320 will now be described.

Figure 9:
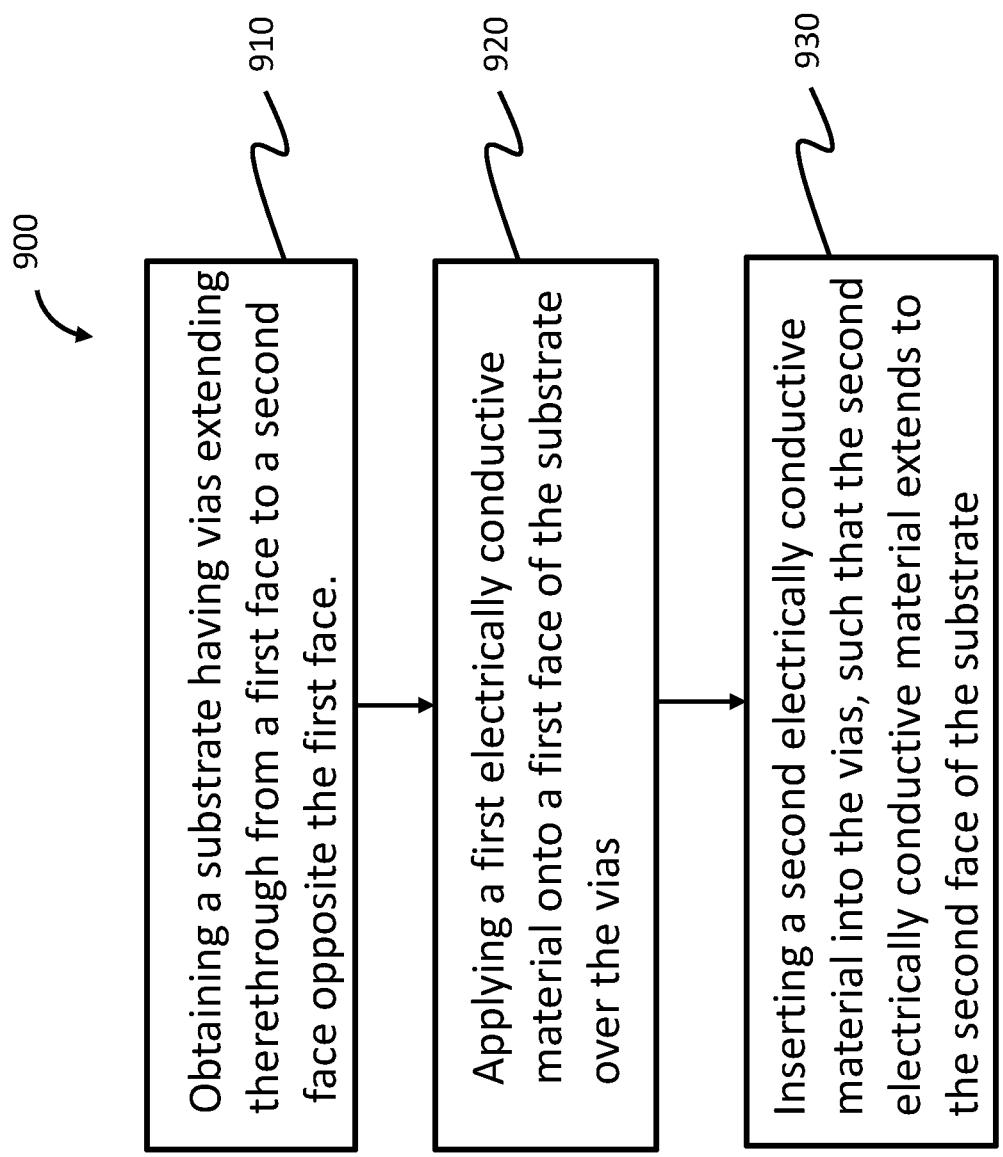
FIG. 9 is another exemplary flow chart for an exemplary method.
Figure 10A:
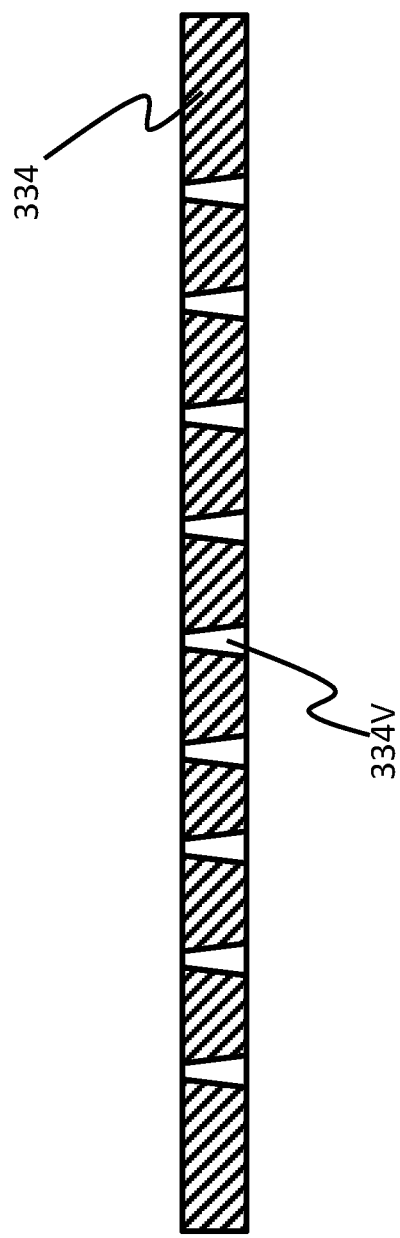
FIG. 10A is a cross-sectional view of an exemplary substrate that can be utilized as part of a housing of an exemplary embodiment.
Figure 10B:
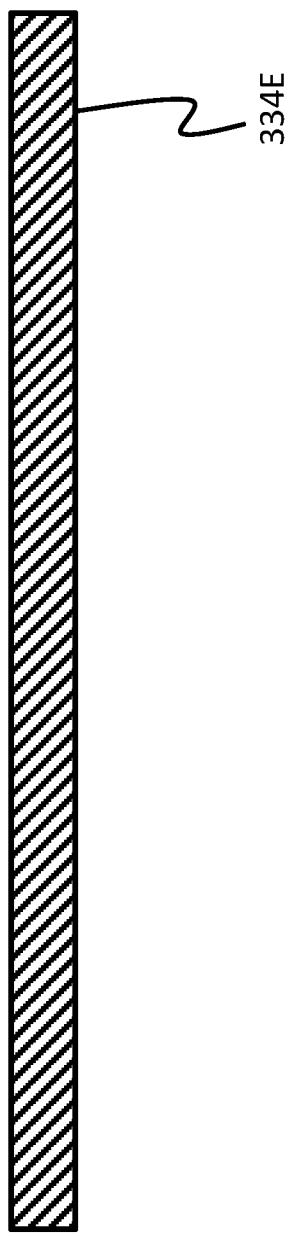
FIG. 10B is a cross-sectional view of an exemplary embryonic substrate that can be utilized as part of a housing of an exemplary embodiment.

FIG. 9 presents an exemplary flowchart for a method 900 of producing a lid including feedthroughs 340 of FIG. 3 (collectively identified by element 315). Method 900 includes method action 910 which entails obtaining a substrate having vias extending therethrough from a first face to a second face opposite the first face. FIG. 10A depicts the result of method action 910 substrate, corresponding to lid 334 of FIG. 9 without the pins 344 in the vias 334V and without the external connection components 342 over the vias 334V. In an exemplary embodiment, the substrate is a sapphire substrate that began as an embryonic substrate 334E as depicted in FIG. 10B. (An exemplary method of executing method action 910 will be described below, entailing the placement of the vias in the embryonic substrate 334E. That said, it is not necessary to place the vias 334V into the substrate 334 to execute method action 910. It is sufficient to obtain a substrate according to FIG. 10A that already has the vias 334V therein.) In an exemplary embodiment, method action 910 corresponds to hermetic bonding of Pt—Al2O3 via hot-pressing a Pt foil onto a sapphire substrate (which can be laser structured, as detailed further below).

Figure 11:
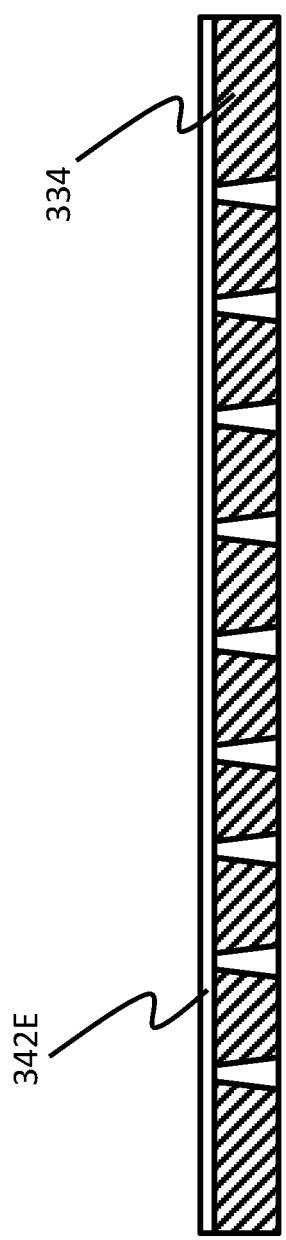
FIG. 11 is a cross-sectional view of an exemplary embryonic component that can be further processed into a component that can utilize as part of a housing according to an exemplary embodiment.

Method 900 further includes method action 920, which entails applying a first electrically conductive material onto a first face of the substrate 334 over the vias 334V. FIG. 11 depicts the result of method action 920, where the first electrically conductive material is a layer 342E corresponding to an embryonic external connection component. In an exemplary embodiment, layer 342A is a platinum layer/comprises platinum. In an exemplary embodiment, method action 920 is executed by hot-pressing a foil of platinum or some other electrically conductive material, onto the first face of the substrate 334.

Figure 12:
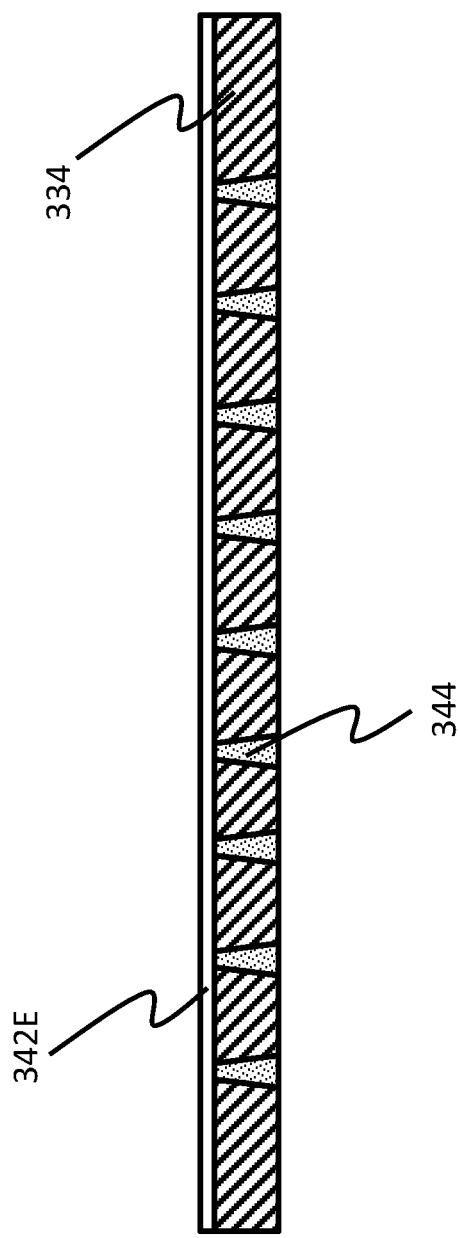
FIG. 12 is a cross-sectional view of another exemplary embryonic component that can be further processed into a component that can utilize as part of a housing according to an exemplary embodiment.

Continuing with reference to FIG. 9, method 900 further includes method action 930, which entails inserting a second electrically conductive material (e.g. silver or platinum) into the vias 334V of the substrate 334, such that the second electrically conductive material extends to the second face of the substrate. FIG. 12 depicts the result of method action 930. In at least some embodiments of method action 930, the action of inserting the second electrically conductive material into the vias 334V results in a hermetic barrier between a first side of the substrate (e.g., the side with the layer 342E) and the second side of the substrate (the side facing away from the layer 342E).

Method action 930 can be executed by, for example, filling the vias 334V with conductive material via electroplating (e.g., silver electroplating). Thus, method 900 results in hermetic bonding of platinum or another utilitarian material to create hermetic feedthroughs in a sapphire substrate, thereby forming the lid of the housing 330 of FIG. 3.

It is noted that in an alternate embodiment, method action 930 can be executed before method action 920.

In an exemplary embodiment, the result of method 900 is that the second electrically conductive material 344 is in electrical communication with the first electrically conductive material 342E (the embryonic external connector component). Also, in an exemplary embodiment, the result of the application of the first electrically conductive material to the substrate 334 and the insertion of the second electrically conductive material in the vias 334V is that at least one via 334V is in electrical communication with another via 334V (due to the embryonic external connector component 342E). This feature will be modified to establish the feedthorughs, as will now be explained.

Figure 13:
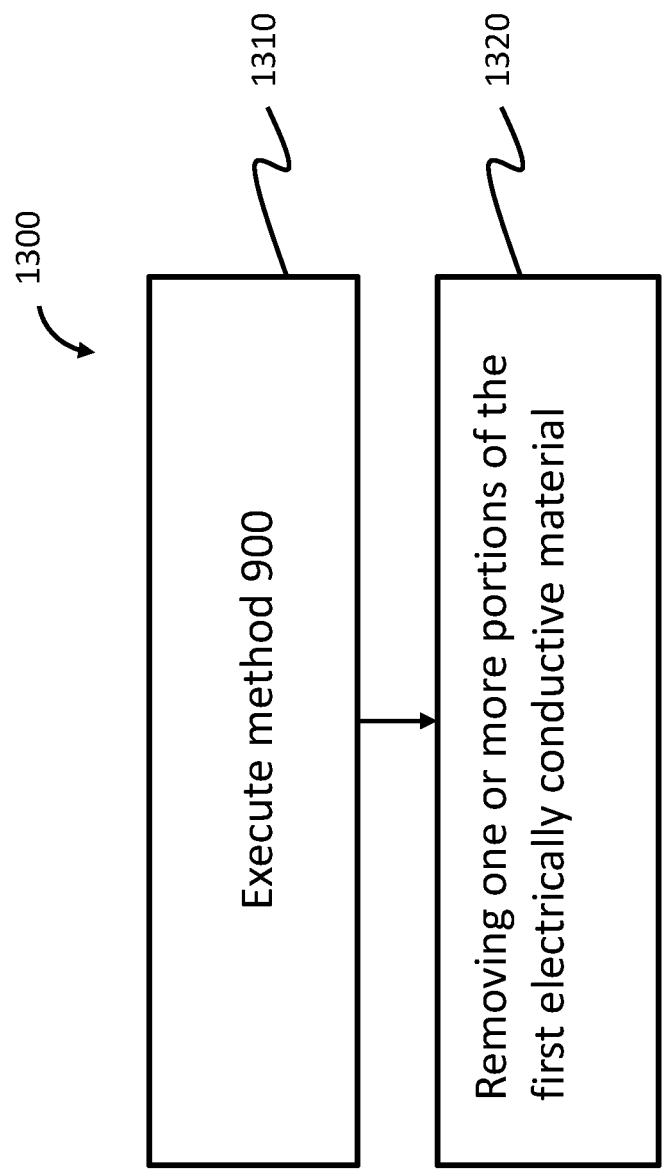
FIG. 13 is another exemplary flow chart for an exemplary method.

FIG. 13 depicts another flowchart for an exemplary method 1300. Method 1300 includes method action 1310, which entails executing method 900 (either by practicing action 920 before or after action 930. Method 1300 further includes method action 1320, which entails removing one or more portions of the first electrically conductive material (e.g., the embryonic external connector component 342E) relative to the vias 334V such that at least one via 334V previously in electrical communication with another via 334V is no longer in electrical communication with that via 334V. In an exemplary embodiment, portions of the first electrically conductive material are removed such that none of the vias 334V are in electrical communication with each other. In an exemplary embodiment, the result of method action 1320 can be seen in FIG. 14 which depicts the lid and the feedthroughs as a single component 315 ready for connection to substrate 332 to establish housing 330 (discussed further below). In an exemplary embodiment, the removal of one or more portions of the first electrically conductive material is accomplished via structuring using laser patterning. That said, alternate actions can be taken to execute method action 1320. Any actions that can enable method action 13202B executed can be utilized in at least some embodiments. Indeed, in this regard, method 1300 can be executed utilizing any actions that can result in any of the devices detailed herein. In this regard, any device, system and/or method that can enable a lid to have a feedthrough/ that can be used to make such a lid, that can enable the teachings detailed herein can be utilized in at least some embodiments.

Figure 14:
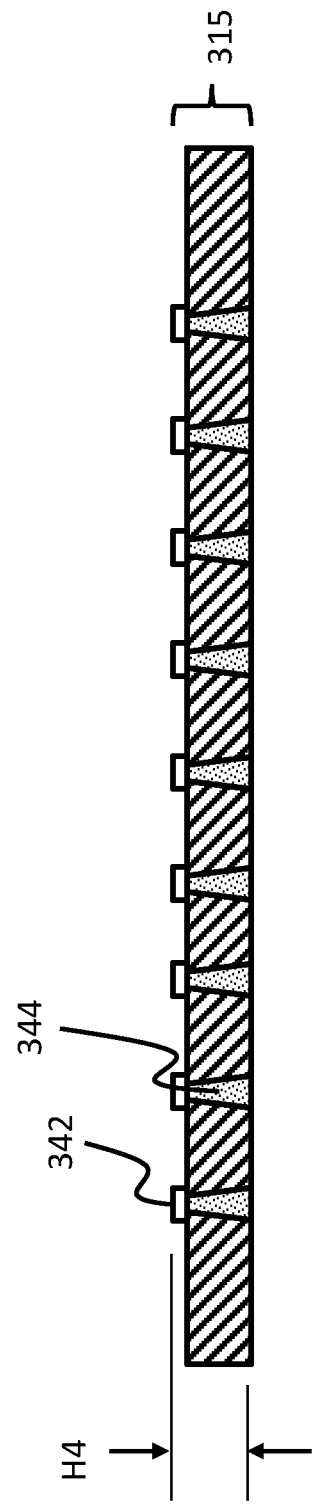
FIG. 14 is a cross-sectional view of a component that can be used as part of a housing according to an exemplary embodiment.

FIG. 14 depicts a height H4, which corresponds to the height of the substrate and feedthrough combination 315 as measured normal to the span-wise direction of the substrate 334 (and through the space 370 when attached to substrate 332). H4 can be, in some embodiments, no more than about 25, 50, 75, 100, 125, 150, 175, 200, 225, 250, 275, 300, 325, 350, 375, 400, 425, 450, 475, 500, 525, 550, 575, 600, 625, 650, 675, 700, 725 or 750 microns or any value or range of values therebetween in about 1 micron increments.

Some exemplary sub-actions and/or alternate actions associated with methods 900 and 1300 will now be briefly detailed.

As noted above, method action 930 can be accomplished by electroplating to create silver pins filling the vias 334V. After that action (or whatever alternate action or additional action is executed to execute method action 930), one or both surfaces (the latter in a scenario where method action 930 is executed prior to method action 920) are polished. In a similar vein, after method action 1320 is executed, one or all of the surfaces of the resulting component 315 can be polished or otherwise subjected to further processing.

Still further, while the embodiment of method action 930 detailed above has been described in terms of electroplating (silver electroplating), in an alternate embodiment, the vias 334V can be filled with a platinum paste or the like (for subsequent co-firing with the substrate, as will be described below, where the first layer 342E is applied via a lamination process subsequently to firing). That is, the action of inserting the second electrically conductive materials into the vias can include inserting an electrically conductive paste (e.g., a platinum paste).

In an exemplary embodiment, the paste is a suspension of platinum particles in an Al2O3 matrix that, when sintered, becomes a solid structure (and thus forms the pin 344). The paste has approximately the same coefficient of thermal expansion as the main body of the Al2O3 substrate (sapphire substrate). This can have utilitarian value in limiting and/or preventing the potential for cracks as the assembly heats and cools (such as during firing, as detailed below).

As noted above, method action 910 entails obtaining a substrate having vias therein. An exemplary method of executing that method action entails cutting vias into a substrate, such as a sapphire substrate. In at least some embodiments, the vias can be made by laser cutting the sapphire substrate or otherwise laser structuring the sapphire substrate. Any device, system and/or method that can enable the establishment of the vias in the substrate can be utilized in at least some embodiments.

Figure 15:
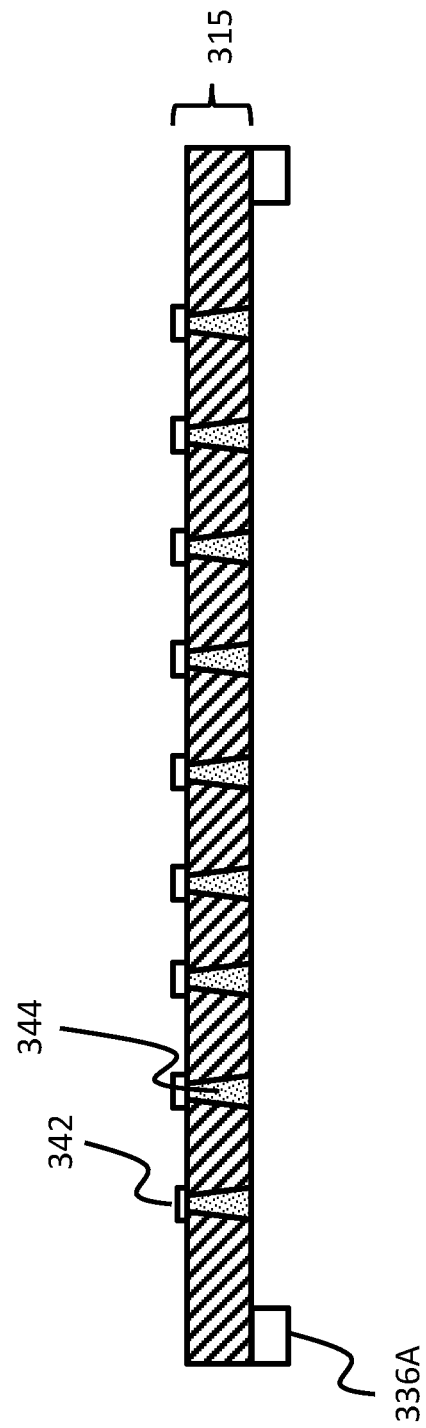
FIG. 15 is a cross-sectional view of the component of FIG. 14 to which is attached side housing components according to an exemplary embodiment.

As noted above with reference to FIG. 3, the housing 330 includes side housing components 336 that serve to span the gap between the lid 334 and the substrate 332. In an exemplary embodiment, side housing components 336 are a combination of components that are respectively initially bonded to the lid 334 and the substrate 332 prior to establishing the hermetic housing 330. Accordingly, an exemplary method includes applying a side housing component 336A at the outer edge of the lid and feedthrough apparatus 315, as can be seen in FIG. 15. In an exemplary embodiment, this is accomplished via chemical vapor deposition (CVD) to create a bonding stack of Ti/Pt/Au at the edges of the substrate 334 opposite the external connector components 342, as seen in FIG. 15. As will be described below, in an exemplary embodiment, the side housing component 336A is bonded or otherwise attached to a corresponding component attached to the substrate 332. That said, in an alternate embodiment, the side housing component 336A can extend all the way to the substrate 332 during assembly, such that no corresponding component attached to the substrate 332 is utilized.

An exemplary method of establishing the substrate 332 and the components associated therewith that are attached to the substrate 334, or more accurately, preparing the substrate and the components associated therewith for attachment to the substrate 334 will now be described.

Figure 16:
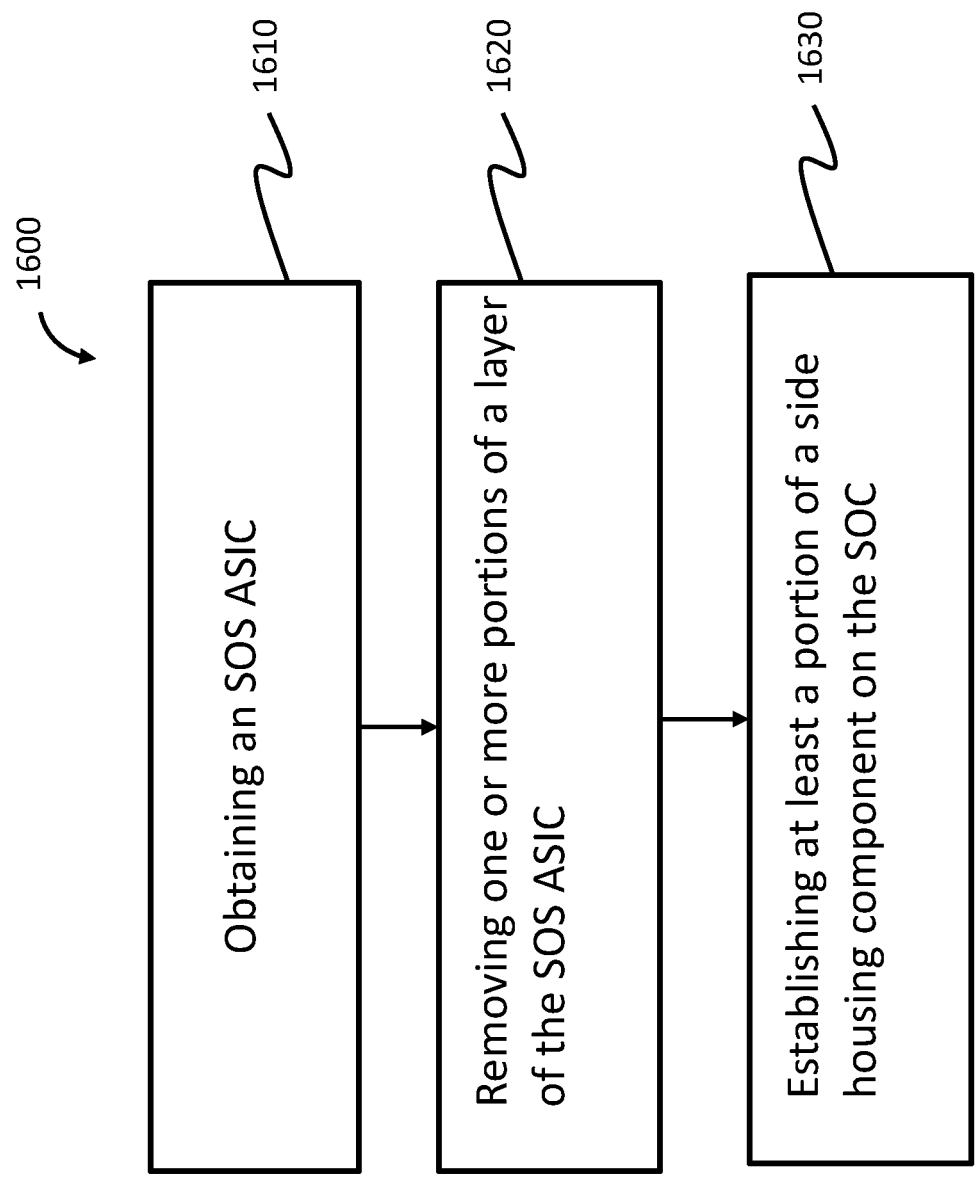
FIG. 16 is another exemplary flow chart for an exemplary method.

FIG. 16 presents an exemplary flow chart for an exemplary method 1600, which includes method action 1610, which entails obtaining an SOS ASIC (such as one that will ultimately correspond to substrate 332 and circuit 350 of FIG. 3).

Figure 17:
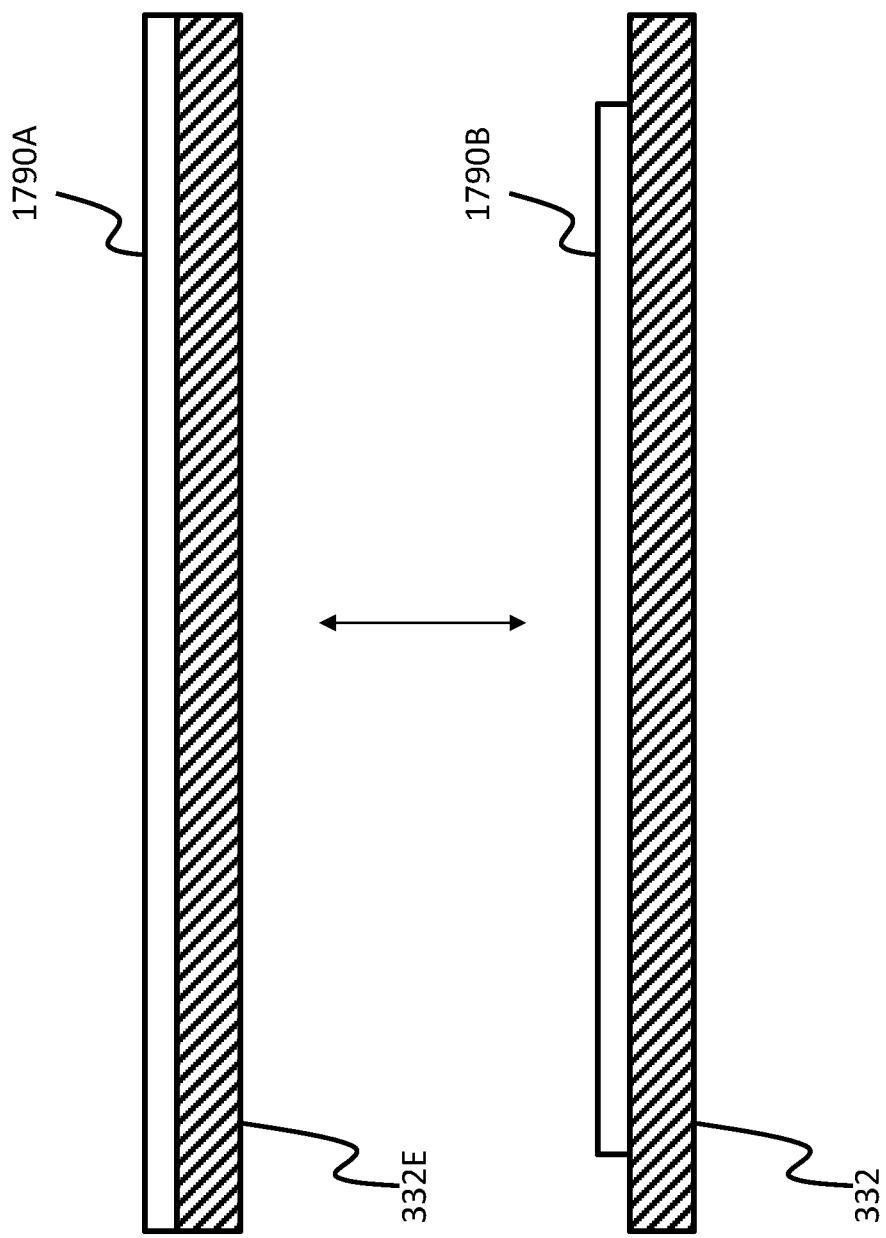
FIG. 17 graphically illustrates a process of converting a substrate according to an exemplary embodiment such that he can be attached to another component to establish a housing according to an exemplary embodiment.

Method 1600 includes method action 1620, which can be an optional method action, which entails removing at least some of the passivation layers from the SOS ASIC, such as the passivation layers at the edges of the substrate 334. Functionally, this is depicted in FIG. 17, where reference numeral 332E corresponds to an embryonic substrate having therein and/or thereon an ASIC, along with a passivation layer 1790, and reference number 332 corresponds to the substrate having the pertinent portions of the passivation layer removed (resulting in passivation layer 1790B), which is ultimately attached to the substrate 334. In an exemplary embodiment, the passivation layers correspond to layers of $SiO_2$ or the like. Method action 1620 can be executed via reactive ion etching. Any device, system and/or method that can enable method action 16202B executed can utilize in at least some embodiments.

Figure 18:
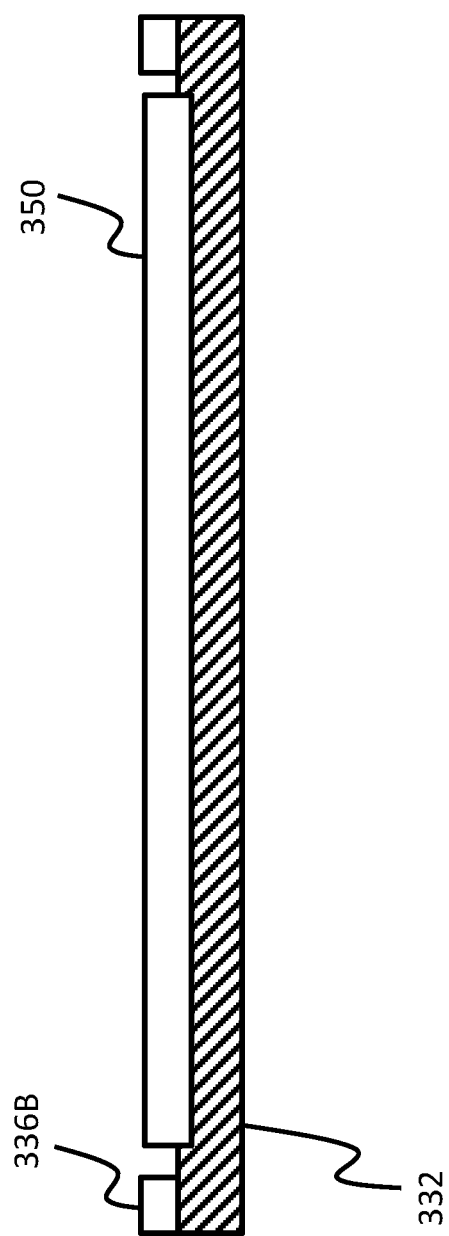
FIG. 18 is a cross-sectional view of an SOS component to which is attached side housing components according to an exemplary embodiment.

Method 1600 further includes method action 1630, which entails establishing at least a portion of the side housing component 336, portion 336B as seen in FIG. 18, on the substrate 332. In an exemplary embodiment, this can be achieved via patterning metallization layers on the edge of the substrate 332 using lithography with CVD and/or other suitable methods, such as by way of example only and not by way limitation, sputtering techniques, electron beam evaporation or plasma enhanced CVD. These metallization layers can be made up of titanium as an adhesion layer to the sapphire substrate 332, thus forming a hermetic interface between the two components. Platinum can be applied to provide a diffusion stop layer for later AuSn reflow soldering. Silver can be added to promote wetting of the AuSn and, in at least some embodiments, provides a relatively rapid diffusive bonding reaction that the ASIC remains on elevated temperatures for a minimum amount of time.

Figure 19:
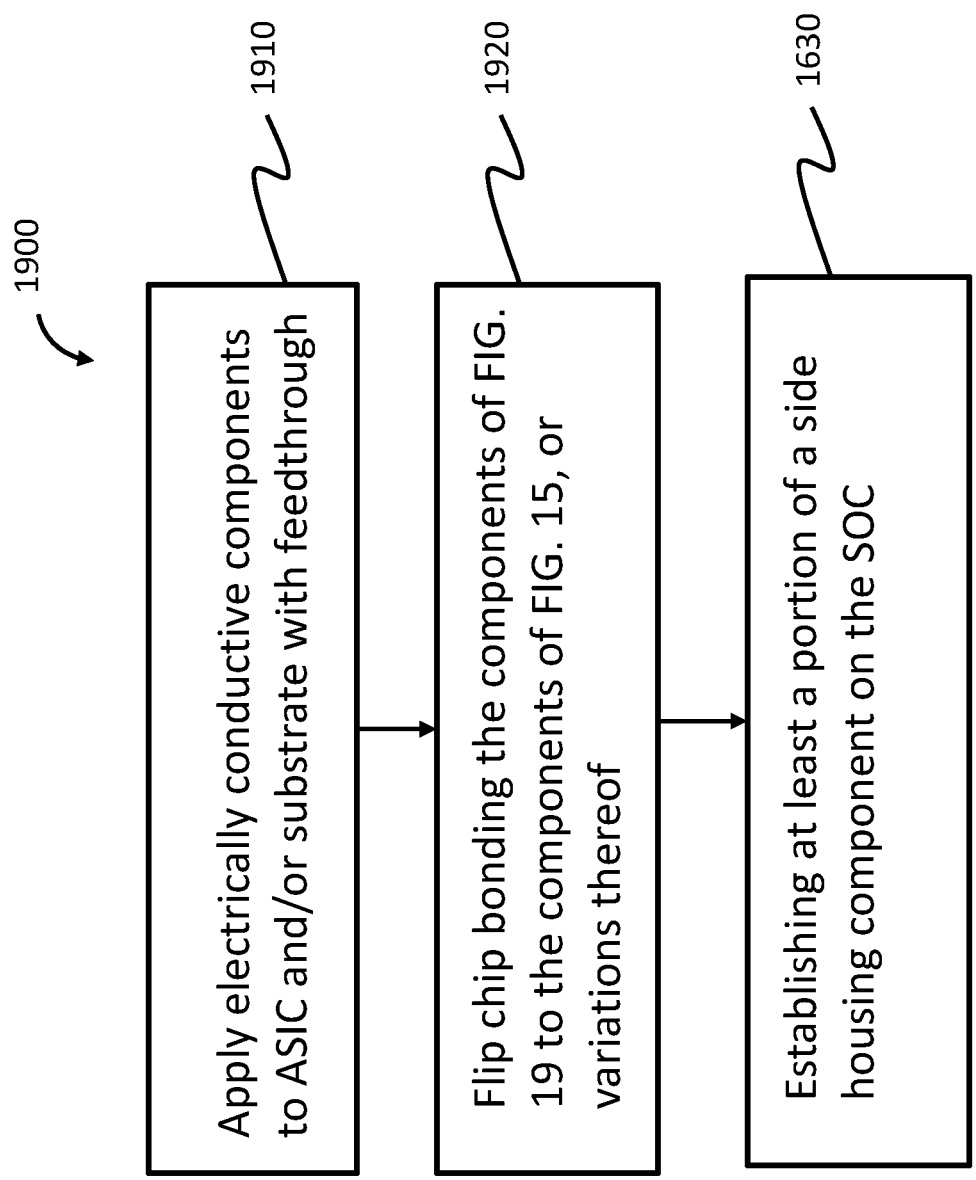
FIG. 19 is another exemplary flow chart for an exemplary method.

In an exemplary embodiment, the side housing component 336B is configured to be attached to side housing component 336A. That said, in an alternate embodiment, side housing component 3368 can be configured to directly attached to the substrate 334 in the absence of side housing component 336B. Any device, system or method of attaching substrate 334 to substrate 332 can be utilized providing the teachings detailed herein and/or variations thereof can be practiced. To this end, FIG. 19 presents an exemplary flowchart for an exemplary method 1900 of joining the components of FIGS. 15 and 18 together (or variations of those components) such that the feedthrough 340 is in electrical communication with the ASIC 350 in/on the substrate 332. More particularly, method 1900 includes method action 1910, which entails applying electrically conductive components to the ASIC 350 and/or the substrate with feedthrough 315. In an exemplary embodiment, method action 1910 is executed by applying stud bumps 380 to the ASIC 350 and/or to the lid and feedthrough 315. In an alternative exemplary embodiment, method action 1910 is establish via extensions of the conductive material in the vias that are configured to connect to the ASIC 350 when the substrates are connected to one another and/or via extensions of the ASIC 350 that extended to the conductive material in the vias when the substrates are connected to one another. Accordingly, in an exemplary embodiment, method action 1910 can be executed by obtaining a substrate having these extensions. Any device, system and/or method that will span a gap between the component supported by the substrate that has the vias (substrate 334) and the integrated circuit (ASIC 350) such that electrical communication is established therebetween can be utilized in at least some embodiments.

Method 1900 further includes method action 1920, which entails flip chip bonding substrate 332 having the integrated circuit 350 at least one of therein or thereon to the substrate 334 (whether or not side housing components 336A and/or 336B are present—i.e., the flip chip bonding is accomplished via direct bonding of the two substrates or indirect bonding of the two substrates via side housing components 336A and/or 336B). In an exemplary embodiment, the results of the flip chip bonding is that the conductive material in the vias of the substrate 334 is an electrical communication with the integrated circuit 350, and a hermetically enclosed volume is established in a space between the two substrates 332 and 334.

In an exemplary embodiment, side housing component 336 corresponds to a seal ring that is created by AuSn soldering controlled environment that results in a relatively limited, if any, residual humidity in the space 370 relative to that which would be the case without the control volume and/or to prevent oxidations during the bonding process. Alternatively and/or in addition to this, ultra-sonic welding can be applied, for instance, to bond silver plating on the two portions of the assembly.

More specifically, an exemplary microelectronic chip usable in at least some embodiments can have aluminum surfaces (pads) onto which wires are bonded in order to establish communication from the chip to external components (e.g., electrodes). An oxide ($Al_2O_3$) can form relatively quickly onto the aluminum. In some instances, this can prevent effective adhesion of solders such as AuSn. In an exemplary embodiment, this is alleviated, at least in part, by etching away the $Al_2O_3$ and depositing another metal (the diffusion stop layer referred to above). Pt is a utilitarnain metal for this stop layer and the addition of Ag onto that can enable utilitarian adhesion (related to wetting) of the solder to the pads.

Accordingly, an exemplary embodiment alleviates at least some of the potential need for executing a specific set of steps in order to etch the $Al_2O_3$ and deposit Pt+Ag, the deposition (at least of the Pt) can be part of the processing of the wafer to establish the "adhesion layer" described above (thereby saving steps).

Some of these features can have utilitarian value with respect to element 380 of FIG. 3, which can be a ball that can be Au, AuSn or several other materials. If AuSn or some other form of "solder" is used, in some instances, it might not stick to the chip without the Pt+Ag (or equivalent) diffusion stopper (Pt) and wetting promoter (Ag). An alliterative embodiment can include element 380 corresponding to an Au ball that is ultrasonically bonded to the pads on 350.

Still further, the Ti adhesion layer is one approach that can establish the adhesion layer. If the material used to establish the adhesion layer is changed to Pt, utilitarian value can be obtained by depositing the diffusion stop layer at the same time as establishing the adhesion layer. Thus, an exemplary embodiment includes executing one or more of the manufacturing actions in one step.

Thus, in view of the above, there is method of producing an encapsulated electronic apparatus, comprising the actions of providing an SOS integrated circuit, forming a base of the encapsulation from the silicon substrate of the SOS integrated circuit, and bonding a lid substrate to the base, the lid substrate comprising sapphire. This method can further comprise the action of providing metallization layers, which can be titanium adhesion layer, to form a hermetic interface between the sapphire structures and the Ti. In an exemplary embodiment, platinum is applied as a metallization layer. In an embodiment, this can provide a diffusion stop layer for later AuSn reflow soldering. In an embodiment, the method comprises the action of adding silver promote wetting of the AuSn and allow for rapid diffusive bonding reaction.

Figure 20:
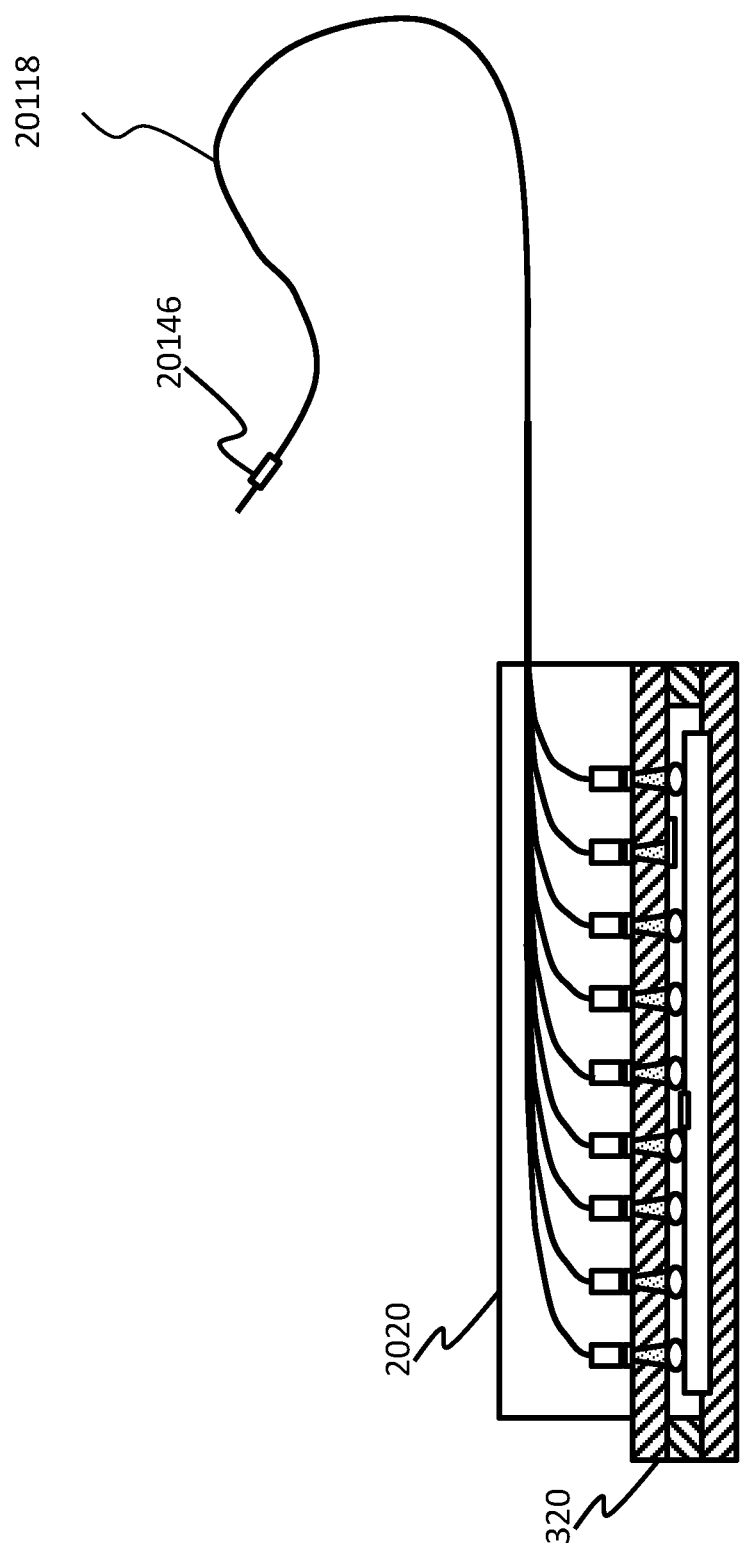
FIG. 20 is an exemplary embodiment of an implantable medical device utilizing the embodiment of FIG. 3.

FIG. 20 depicts an exemplary quasi-functional schematic of an implantable component of a cochlear implant corresponding to that of FIG. 1 above. As can be seen, a connector 2020 is attached to the encapsulated electronic circuits 320. The connector 2020, in combination with a lead component of 20118, which corresponds to the electrode assembly 118 of FIG. 1 (where element 20146 corresponds to the distally extending array 146 of electrodes 148), establishes a bus between the feedthrough 340 and the array 20146. In the embodiment of FIG. 20, the connector 2020 is configured to attach to the outside of the encapsulated electronic circuit 20202 establish and maintain an electrical connection between the bus and the external connector components 342, thereby placing the electrodes of the array 20146 into electrical communication with the hardware located inside the encapsulated electronic circuit 320.

While the embodiment of FIG. 20 is depicted in terms of a cochlear electrode array, other embodiments can utilize the connector 20202 place another component of an implantable prosthesis into electronic communication with the hardware of the encapsulated electronic circuit 320.

In an exemplary embodiment, connector 2020 and/or encapsulated electronic circuit 320 is/are configured to provide a seal to at least limit, if not prevent, ingress of body fluids to the external connector components 342.

Figure 21:
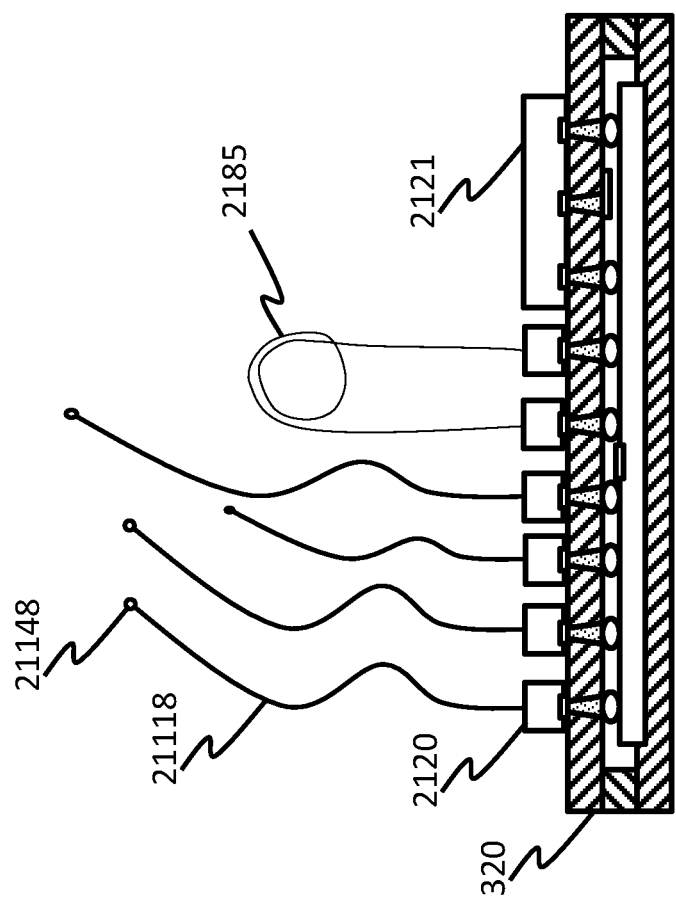
FIG. 21 is another exemplary embodiment of an implantable medical device utilizing the embodiment of FIG. 3.

FIG. 21 depicts an exemplary quasi-functional schematic of an implantable component having individual electrodes 21148 having individual leads 21118. As can be seen, respective connectors 2120 for each individual lead-electrode combination is attached to the encapsulated electronic circuits 320. The connectors 2120, in combination with the respective leads 21118, establishes a bus between the feedthrough 340 and the electrodes 21148. In the embodiment of FIG. 21, the connectors 2120 are configured to attach to the outside of the encapsulated electronic circuit to establish and maintain an electrical connection between the respective busses of the respective electrodes 21148 and the respective external connector components 342, thereby placing the electrodes 21148 into electrical communication with the hardware located inside the encapsulated electronic circuit 320. In an exemplary embodiment, the embodiment of FIG. 21 can correspond to a pacemaker or a muscle stimulator or the like (although more or fewer electrode-lead combinations may be present than that depicted in FIG. 21).

In an exemplary embodiment, connectors 2120 and/or encapsulated electronic circuit 320 is/are configured to provide respective seals to at least limit, if not prevent, ingress of body fluids to the external connector components 342.

Also, the embodiment of FIG. 21 enables a plurality of different functional components having different functionalities to be placed into communication with the encapsulated electronic circuit 320. As can be seen, telecoil 2185 is connected via two connectors 2120 to the circuit 320. Telecoil can be used for wireless communication (e.g., inductive communication) with the encapsulated electronic circuit 320. Alternatively or in addition to this, element 2185 can be used to transcutaneously transmit power to the encapsulated electronic circuit 320.

As can be seen, not all of the external connector components 342 are in communication with an electrode (or electrode lead). In this regard, a cap 2121 is located over the unused external connector components as can be seen. In an exemplary embodiment, cap(s) 2121 and/or encapsulated electronic circuit 320 is/are configured to provide a seal to at least limit, if not prevent, ingress of body fluids to the external connector components 342 covered by the cap 2121. Thus, cap 2121 permits flexibility with respect to how many electrodes are to be utilized with the encapsulated electronic circuit 320, thereby enabling a given production run of encapsulated electronic circuits 320 to be used in various applications without having to redesign/reengineer the encapsulated electronic circuit 320.

Figure 22:
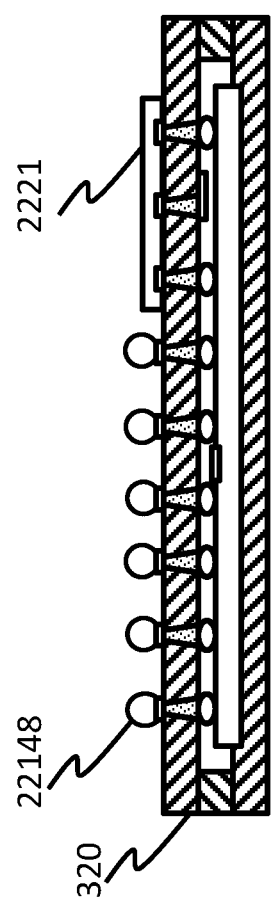
FIG. 22 is another exemplary embodiment of an implantable medical device utilizing the embodiment of FIG. 3.

FIG. 22 depicts another exemplary quasi-functional schematic of an implantable component having individual electrodes 22148 directly connected to the external connector components 342, establishing and maintaining an electrical connection between the electrodes 22148 and the respective external connector components 342, thereby placing the electrodes 21148 into electrical communication with the hardware located inside the encapsulated to a pacemaker or a muscle stimulator or the like (although more or fewer electrode-lead combinations may be present than that depicted in FIG. 22).

As can be seen, a cap 2221, which has a lower profile than cap 2121, to provide more room for the electrodes 22148, covers unused components 342.

In an exemplary embodiment, the components 342 (and thus the vias) can be patterned in a desired pattern such that the electrodes 22148 will have the corresponding pattern.

An exemplary embodiment includes a plurality of micro-IMD arranged in a multi-unit device where the units are operated in master slave modes. Such an exemplary embodiment can allow for recording and stimulating at multiple sites of neural tissue, or for a larger main power and signal supply unit to be implanted away from the stimulation sites with smaller "satellite" units placed closer to the stimulation sites, interfaced by a small number of wires for the delivery of power and data to the satellite devices.

Typically, different types of implantable medical devices are manufactured independently using separate production lines. As one example, cochlear implants and middle-ear implants (DACIs) are two types of implantable hearing prosthesis that are typically manufactured on separate production lines. As an additional example, a combination implantable hearing prosthesis that includes both a cochlear implant electrode assembly and a middle-ear implant transducer may conventionally be manufactured on a separate production line from cochlear implants and middle-ear implants. An encapsulated electronic circuit in accordance with the teachings detailed herein and/or variations thereof can serve as the electronics module for any one of a plurality of different types of hearing prostheses, including each of the hearing prostheses mentioned above. As such, a single production line for manufacturing a device that can be used as a universal implant in accordance with the teachings detailed herein and/or variations thereof can replace a significant portion of each of the production lines of various conventional hearing prostheses.

An exemplary embodiment, utilizing the same material, or at least similar material for the substrate 332, and the lid 334, results are respective components with similar coefficient of thermal expansion. This can allow for a theoretically "perfect" CTE match and/or can result in reduction and/or elimination of stresses in the assembly from temperature shocks and cycles.

In an exemplary embodiment, the encapsulated electronic circuit 320 includes relatively little, and, in some embodiments, no underfill material that might otherwise be utilized for stabilization of the electronic circuit (ASIC 350), because the ASIC is integrated in the substrate and forms part of the encapsulation. In an exemplary embodiment, problems associated with stabilization are reduced and/or eliminated and mechanical stabilization is provided by the sealing ring (side housing 336). In an exemplary embodiment, encapsulated electronic circuits 320 that include no underfill can have some utilitarian value. For example, the hermeticity sensor components can be integrated into the free space, which, in some embodiments, is only a few 10 s or 100 s of micrometers tall. The volume 370 can act as a buffer for water molecules, which may enter the cavity over time. More specifically, because of the specific size of the space, the formation of water droplets is delayed relative to that which would be the case for smaller sized volumes, and failure modes due to moisture ingress, such as by way of example only and not by way limitation, corrosion, are reduced, again relative to larger sized volumes. humidity in the volume is higher for a given amount of fluid ingress (e.g., water, human body fluid, etc.), and thus the internal sensor (e.g., humidity sensor) is more likely to be activated than would otherwise be the case for a smaller sized volume. By smaller sized volumes, it is meant volumes that are about, one half, one fourth, one eighth, one tenth, one fifteenth, one twentieth, one twenty-fifth, one thirtieth, one fiftieth or about one hundredth or any value or range of values from 0.5 to 0.01 or any value therebetween in 0.01 increments times smaller than one or more or all of the volumes detailed herein.

The avoidance of underfill can also prevent failure modes such as chip delamination due to moisture-induced swelling of the underfill. Moreover, the temperature profile during AuSn sealing is any more flexible relative to that which would be the case if underfills were utilized as underfills can limit the processing time due to degradation limitations of the epoxy material.

Hermeticity testing can be simplified relative to that which would be the case utilizing underfills because polymers are avoided. Polymers can impede measurement signals, either by blocking or diffusing optical beam paths (in embodiments where the sensor 360 utilizes an optical sensor), or by increasing the signal to noise ratio in molecular sensors (in embodiments where the sensor 360 utilizes such). By avoiding the utilization of polymers, these deleterious effects can be reduced and/or eliminated. Further in this regard, polymers can absorb trace gasses (e.g. hydrogen, water vapor, etc). Accordingly, over time, a polymer can outgas into the volume 370 (e.g., because of the difference in vapor pressure inside the volume 370). This could appear as a leak, even though there is no leak.

In at least some embodiments, the teachings detailed herein and variations thereof results in packaging that can enable ultrasmall volume, hermetic encapsulations that have utilitarian value for medical devices (and other applications).

In at least some embodiments, the teachings detailed herein and or variations thereof results in a encapsulated electronic circuit 320 where interference resulting from metallic surfaces are reduce and/or eliminated, which enables the inclusion of wireless power and data transfer using integrated induction circuitry on ASIC. Moreover, the transparent surfaces of the SOS permits for data and/or power to be transmitted optically. Accordingly, in an exemplary embodiment includes a method of transmitting data and/or power optically through walls of the housing 330 without having to modify the housing walls/create a path for the transmitted data/power through the wall. Still further, in at least some exemplary embodiments, there is an apparatus that includes a device configured to optically communicate power and/or data through the housing without having a path for the transmitted data/power through the wall.

Some embodiments of the teachings detailed herein enable a single connection to provide a plurality of electrical signal routes via a single connection between an auxiliary component (e.g., a multi electrode (22 electrode) electrode array of a cochlear implant) and the encapsulated electronic circuit 320. In an exemplary embodiment, this can enable a relatively high number of electrical signal paths over a given area as compared to that which would be the case in the absence of the teachings detailed herein. By way of example only and not by way of limitation, about 2, 3, 4, 5, 6, 7, 8, 9, 10, 11, 12, 13, 14, 15, 16, 17, 18, 19, 20, 25, 30, 40, 50, 60, 70, 80 90 or about 100 paths (e.g., contacts) per mm2 or any value or range of values therebetween in 1 increment can be achieved and thus used in some embodiments.

In an exemplary embodiment, power transfer to and/or from the encapsulated electronic circuit 320 and/or communications with the encapsulated electronic circuit 320 can be performed wirelessly. By way of example only and not by way limitation, in an exemplary embodiment, the communication can be performed utilizing inductive link where the implant inductor is integrated on the ASIC 350.

It is noted that any disclosure with respect to one or more embodiments detailed herein can be practiced in combination with any other disclosure with respect to one or more other embodiments detailed herein.

It is noted that some embodiments include a method of utilizing a prosthesis including one or more or all of the teachings detailed herein and/or variations thereof. In this regard, it is noted that any disclosure of a device and/or system herein also corresponds to a disclosure of utilizing the device and/or system detailed herein, at least in a manner to exploit the functionality thereof. Further, it is noted that any disclosure of a method of manufacturing corresponds to a disclosure of a device and/or system resulting from that method of manufacturing. It is also noted that any disclosure of a device and/or system herein corresponds to a disclosure of manufacturing that device and/or system.

While various embodiments have been described above, it should be understood that they have been presented by way of example only, and not limitation. It will be apparent to persons skilled in the relevant art that various changes in form and detail can be made therein without departing from the scope of the invention. Thus, the breadth and scope of the present invention should not be limited by any of the above-described exemplary embodiments, but should be defined only in accordance with the following claims and their equivalents.

What is claimed is:

1. A device, comprising:
an implantable housing configured to establish a hermetic volume therein, wherein the device is configured to enable hermeticity testing via active sensing of one or more phenomena in the hermetic volume; and
a hermeticity sensor component at least one of internal or integral to the housing, wherein the hermeticity sensor component is configured to enable active sensing of the one or more phenomena, thereby enabling the hermeticity testing, wherein
the hermeticity sensor component enables the evaluation of a physical phenomenon associated with at least one of an electrical capacitance or an electrical resistance of a structure exposed to the volume, and enables an output of a signal indicative of a change in the physical phenomenon, thereby indicating a change in a status of hermeticity of the volume, and
the device includes a substrate at least one of in which or on which is located an interdigitized exposed pattern corresponding to the structure exposed to the volume.

2. The device of claim 1, wherein
the device includes an electronic component, and wherein the entire device is an implantable device implantable in a person.

3. An assembly, comprising:
the device of claim 1; and a test apparatus configured to test for leakage from the hermetic volume.

4. A device, comprising:
an implantable housing configured to establish a hermetic volume therein, wherein the device is configured to enable hermeticity testing via active sensing of one or more phenomena in the hermetic volume; and
a palladium wire exposed to the hermetic volume, wherein the palladium wire is in electrical communication with a location on the housing exposed to an ambient environment of the housing.

5. The device of claim 4, wherein the device includes one or more electrical interfaces integral with the housing, the one or more electrical interfaces corresponding to the location on the housing exposed to an ambient environment.

6. The device claim 4, wherein
the housing is part of an apparatus that establishes a rigid structure totally encompassing the hermetic volume.

7. A method, comprising:
obtaining a substrate having vias extending therethrough from a first face of the substrate to a second face of the substrate opposite the first face;
applying a first electrically conductive material onto the first face of the substrate over the vias; and
inserting a second electrically conductive material into the vias, such that the second electrically conductive material extends to the second face of the substrate, wherein
the second electrically conductive material is in electrical communication with the first electrically conductive material, and
the method further comprises making an implantable housing configured to establish a hermetic volume therein wherein the implantable housing is part of a device configured to enable hermeticity testing via active sensing of one or more phenomena in the hermetic volume by attaching a component to the substrate, thereby establishing the implantable housing in a manner that the substrate corresponds to a wall of the implantable housing.

8. The method of claim 7, wherein:
the action of inserting the second electrically conductive material into the vais results in a hermetic barrier between a first side of the substrate and the second side of the substrate.

9. The method of claim 7, wherein:
the action of applying the first electrically conductive material includes hot-pressing a foil, corresponding to the electrically conductive material, onto the first face of the substrate.

10. The method of claim 7, wherein:
the action of inserting the second electrically conductive material into the vias includes filling the vias with conductive material via electroplating.

11. The method of claim 7, wherein:
the action of inserting the second electrically conductive materials into the vias includes inserting an electrically conductive paste, thereby, along with the action of pressing the first electrically conductive material, establishing an embryonic feedthrough, the method further comprising:
firing the embryonic feedthrough.

12. A device, comprising:
an implantable housing configured to establish a hermetic volume therein, wherein the device is configured to enable hermeticity testing via active sensing of one or more phenomena in the hermetic volume, wherein
the housing includes vias extending through a wall of the housing from a first face of the wall to a second face opposite the first face,
a first electrically conductive material is located on the first face of the wall over the vias,
a second electrically conductive material extends through the vias, such that the second electrically conductive material extends to the second face of the wall, and
the second electrically conductive material is in electrical communication with the first electrically conductive material.

13. The device of claim 12 wherein:
the second electrically conductive material establishes a hermetic barrier between a first side of the wall and the second side of the wall.

14. The device claim 12, further comprising:
a hermeticity sensor component at least one of internal or integral to the housing, wherein the hermeticity sensor component is configured to enable active sensing of the one or more phenomena, thereby enabling the hermeticity testing.

15. The device of claim 14, wherein:
the hermeticity sensor component enables the evaluation of a physical phenomenon associated with at least one of an electrical capacitance or an electrical resistance of a structure exposed to the volume, and enables an output of a signal indicative of a change in the physical phenomenon, thereby indicating a change in a status of hermeticity of the volume.

16. The device of claim 15, wherein:
the device includes a substrate at least one of in which or on which is located an interdigitized exposed pattern corresponding to the structure exposed to the volume.

17. The device claim 12, wherein
an implantable electronic circuit is integrated at least one of in or on a substrate, wherein the substrate forms at least a portion of the housing.

18. The device of claim 17, wherein:
the volume is an air-gap between a surface of the substrate and a surface of an adjacent wall of the housing opposite the surface of the substrate, and wherein a height of the housing as measured normal to a spanwise direction of the substrate and through the air-gap is no more than about 1,000 microns.

* * * * *